(12) United States Patent
Verebelyi

(10) Patent No.: US 12,714,609 B2
(45) Date of Patent: Aug. 25, 2026

(54) COMPRESSION SOCK WITH INTEGRATED DONNING AND DOFFING AID SYSTEM

(71) Applicant: David M. Verebelyi, Englewood, CO (US)

(72) Inventor: David M. Verebelyi, Englewood, CO (US)

( * ) Notice: Subject to any disclaimer, the term of this patent is extended or adjusted under 35 U.S.C. 154(b) by 0 days.

(21) Appl. No.: 19/084,396

(22) Filed: Mar. 19, 2025

(65) Prior Publication Data

US 2025/0275874 A1 Sep. 4, 2025

Related U.S. Application Data

(63) Continuation-in-part of application No. PCT/US2024/046925, filed on Sep. 16, 2024.
(Continued)

(51) Int. Cl.
*A61F 13/00* (2024.01)
*A41B 11/00* (2006.01)
*A61F 13/06* (2006.01)

(52) U.S. Cl.
CPC .............. *A61F 13/06* (2013.01); *A41B 11/00* (2013.01); *A41D 2400/44* (2013.01)

(58) Field of Classification Search
CPC ... A61F 2/2475; A41B 2400/44; A41B 11/00; A41B 11/003; A41B 11/02; A41B 2400/32; A41B 11/14; A41B 11/08; A41B 2400/38; A41B 2500/10; A41B 11/12; A41B 2400/80; A41B 11/123; A61H 9/0078; A61H 2201/165; A61H 2205/106; A61H 9/0092; A61H 2205/10; A61H 1/008; A61H 2201/1697; A61H 2201/5071; A61H 2201/164; A61H 2201/5007; A61H 2205/108; A61H 2201/5097; A61H 2201/0103; A61H 2201/0207; A61H 2205/12; A61H 7/001; A61H 2201/1635; A61H 2201/1207; A61H 2201/501;
(Continued)

(56) References Cited

U.S. PATENT DOCUMENTS 5,520,630 A * 5/1996 Daneshvar ............ A61F 15/006
128/DIG. 15
D747,601 S * 1/2016 Middleton ..................... D2/980
(Continued)

FOREIGN PATENT DOCUMENTS

CN 1575156 A * 2/2005 ............ A61F 13/08
DE 202011103221 U1 11/2011

OTHER PUBLICATIONS

CN 1575156 A (translation_ (Year: 2005).*
(Continued)

*Primary Examiner* — Kim M Lewis
(74) *Attorney, Agent, or Firm* — Galvani Smith PLLC

(57) ABSTRACT

A compression sock may include a body comprising an inner face and an outer face, the inner face configured to interface with a wearer's anatomy, the body further comprising: a forefoot region, a midfoot region, a hindfoot region, a tendon region, a shin region; and a calf region. The compression sock may further include a plurality of sequential pulls coupled to the outer face of the body, at least one pull located proximal each region. Each pull may be configured to generate leverage for the wearer donning and doffing the compression sock.

7 Claims, 24 Drawing Sheets

Related U.S. Application Data

(60) Provisional application No. 63/538,680, filed on Sep. 15, 2023.

(58) Field of Classification Search

CPC ...... A61H 2201/5002; A61H 2011/005; A61H 2201/5084; A61H 2201/1642; A61H 2201/5061; A61H 2205/06; A61H 11/00; A61H 2201/1238; A61H 2201/10; A61H 2201/1215; A61H 2201/0157; A61H 2201/0214; A61H 2201/5056; A61H 2201/50; A61H 2201/0192; A61H 2201/5043; A61H 9/0007; A61H 9/005; A61H 2201/5012; A61H 9/00; A61H 2201/169; A61H 23/02; A61H 2201/0228; A61H 31/006; A61H 2230/065; A61H 31/005; A61H 2201/0184; A61H 2201/5082; A61H 39/04; A61H 2201/5035; A61H 2201/5046; A61H 1/0266; A61H 2205/084; A61H 1/00; A61H 1/006; A61H 2230/045; A61H 2201/5058; A61H 2201/5064; A61H 2201/02; A61H 2201/5015; A61H 7/007; A61H 2201/1409; A61H 2201/1654; A61H 31/008; A61H 2201/5048; A61H 2230/50; A61H 2203/0456; A61H 2201/5038; A61H 2203/0406; A61H 2201/1645; A61H 2201/0173; A61H 2201/5069; A61H 2230/208; A61H 2230/625; A61H 2201/1628; A61H 2203/0431; A61H 2205/102; A61H 2230/505; A61H 2201/5005; A61H 2230/60; A61H 2201/5092; A61H 2205/065; A61H 2230/655; A61H 9/0085; A61H 2201/1621; A61H 2201/1695; A61H 2201/0107; A61H 2201/0119; A61H 2201/0142; A61H 2201/0242; A61H 2201/1676; A61H 2201/5074; A61H 2230/06; A61H 9/0057; A61H 2201/1619; A61H 2205/125; A61H 2230/255; A61H 7/00; A61H 9/0071; A61H 99/00; A61H 2201/0134; A61H 23/00; A61H 2201/0257; A61H 2201/1246; A61H 2205/081; A61H 2201/149; A61H 2201/5023; A61H 2201/5025; A61H 2201/5089; A61H 2230/085; A61H 3/00; A61H 2201/0176; A61H 2201/105; A61H 2205/067; A61H 2230/305; A61H 2201/1253; A61H 2201/0149; A61H 2201/5028; A61H 2205/062; A61H 23/0263; A61H 23/04; A61H 31/00; A61H 2205/02; A61H 2207/00; A61H 2230/04; A61H 1/001; A61H 1/0237; A61H 2003/043; A61H 2023/002; A61H 2201/0278; A61H 2205/08; A61H 2230/85; A61H 23/0245; A61H 31/007; A61H 33/14; A61H 36/00; A61H 2201/0146; A61H 2201/018; A61H 2201/5066; A61H 2203/0443; A61H 31/004; A61H 2023/045; A61H 2201/1261; A61H 2201/1638; A61H 2201/1664; A61H 2230/25; A61H 23/006; A61H 1/02; A61H 1/024; A61H 2201/0169; A61H 2201/1418; A61H 2201/168; A61H 2230/08; A61H 23/0254; A61H 1/0255

USPC ........................................................... D2/980

See application file for complete search history.

(56) References Cited

U.S. PATENT DOCUMENTS

| | | | | |
|---|---|---|---|---|
| 11,717,033 | B2 * | 8/2023 | Giorgi | D04B 1/108 66/178 R |
| 2009/0137938 | A1 * | 5/2009 | Parivash | A61F 13/08 602/63 |
| 2010/0006609 | A1 | 1/2010 | McAllister et al. | |
| 2017/0354543 | A1 | 12/2017 | Mazourik et al. | |
| 2020/0205481 | A1 * | 7/2020 | Amis | D04B 1/18 |
| 2021/0068471 | A1 * | 3/2021 | Giorgi | D04B 1/26 |

OTHER PUBLICATIONS

DE 20 2011 103 221 U1 Translation (Year: 2011).*

International Search Report and Written Opinion for Application No. PCT/US2024/046925, mailed on Dec. 2, 2024, 12 pages.

* cited by examiner

COMPRESSION SOCK WITH INTEGRATED DONNING AND DOFFING AID SYSTEM

CROSS REFERENCE TO RELATED APPLICATIONS

This application is a continuation-in-part of the pending International Application No. PCT/US2024/046925 filed Sep. 16, 2024, which claims the benefit of U.S. Provisional Patent Application No. 63/538,680 filed on Sep. 15, 2023, the contents of which are all incorporated herein by reference in their entireties.

TECHNICAL FIELD

The present disclosure generally relates to compression socks. More particularly, it relates to compression socks having an integrated donning and doffing aid system.

BACKGROUND

Medical grade compression socks are a staple treatment for multiple different medical issues. Most commonly, they are used by patients struggling with venous reflux resulting in lower leg swelling, skin changes and ulcerations. Venous reflux affects at least 40% of the population over the age of 65. Compression socks are highly effective in improving symptoms and mobility associated with venous disorders such as edema, phlebitis, and thrombosis. These elastic garments compress the limb, applying significant pressure to reduce vein diameter and increase blood flow. The goal of compression socks is to compress the surface veins, arteries, and muscles to narrow channels, increasing blood circulation throughout the body and preventing blood pooling in the lower limbs. However, given that the socks use much stronger elastics than basic everyday socks, these garments can be exceedingly difficult to put on and grip, especially for the elderly population and the medical professionals who assist them. This is especially so when the compression sock must be pulled over sharp angles, irregular shapes, and rigid protruding bones and tendons. Typical aids include rubberized gloves to aid in gripping the garment, wire structures to pre-stretch the garment and low friction sleeves to pull the sock over the heel. Some of these aids are incompatible with close-toed socks.

SUMMARY

In some aspects, the techniques described herein relate to a compression sock configured to be worn by a wearer, including: a body including an inner face and an outer face, the inner face configured to interface with a wearer's anatomy, the body further including: a forefoot region; a midfoot region; a hindfoot region; a tendon region; a shin region; and a calf region; and a plurality of sequential pulls coupled to the outer face of the body, at least one pull located proximal each region, and wherein each pull is configured to generate leverage for the wearer donning and doffing the compression sock.

In some aspects, the techniques described herein relate to a compression sock configured to be worn by a wearer, including: a body including an inner face and an outer face, the inner face configured to interface with a wearer's anatomy, the body further including: a forefoot region; a midfoot region; a hindfoot region; a tendon region; a shin region; and a calf region; wherein the outer face of the body defines a plurality of sequential openings, at least one opening located proximal each region, and wherein each opening is configured to generate leverage for the wearer donning and doffing the compression sock.

In some aspects, the techniques described herein relate to an integrated compression sock aid that optimizes the friction between the sock and the wearer's skin at key catch points along the wearer's leg, such that the compression sock is easy to don while still maintaining compression integrity after donning.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter of the application and uses of such embodiments. As used herein, the words "exemplary" and "example" mean "serving as an example, instance, or illustration." Any implementation or embodiment described herein as exemplary, or an example is not necessarily to be construed as preferred or advantageous over other implementations. Furthermore, there is no intention to be bound by any expressed or implied theory presented in the preceding technical field, background, or the following detailed description.

Figure 1:
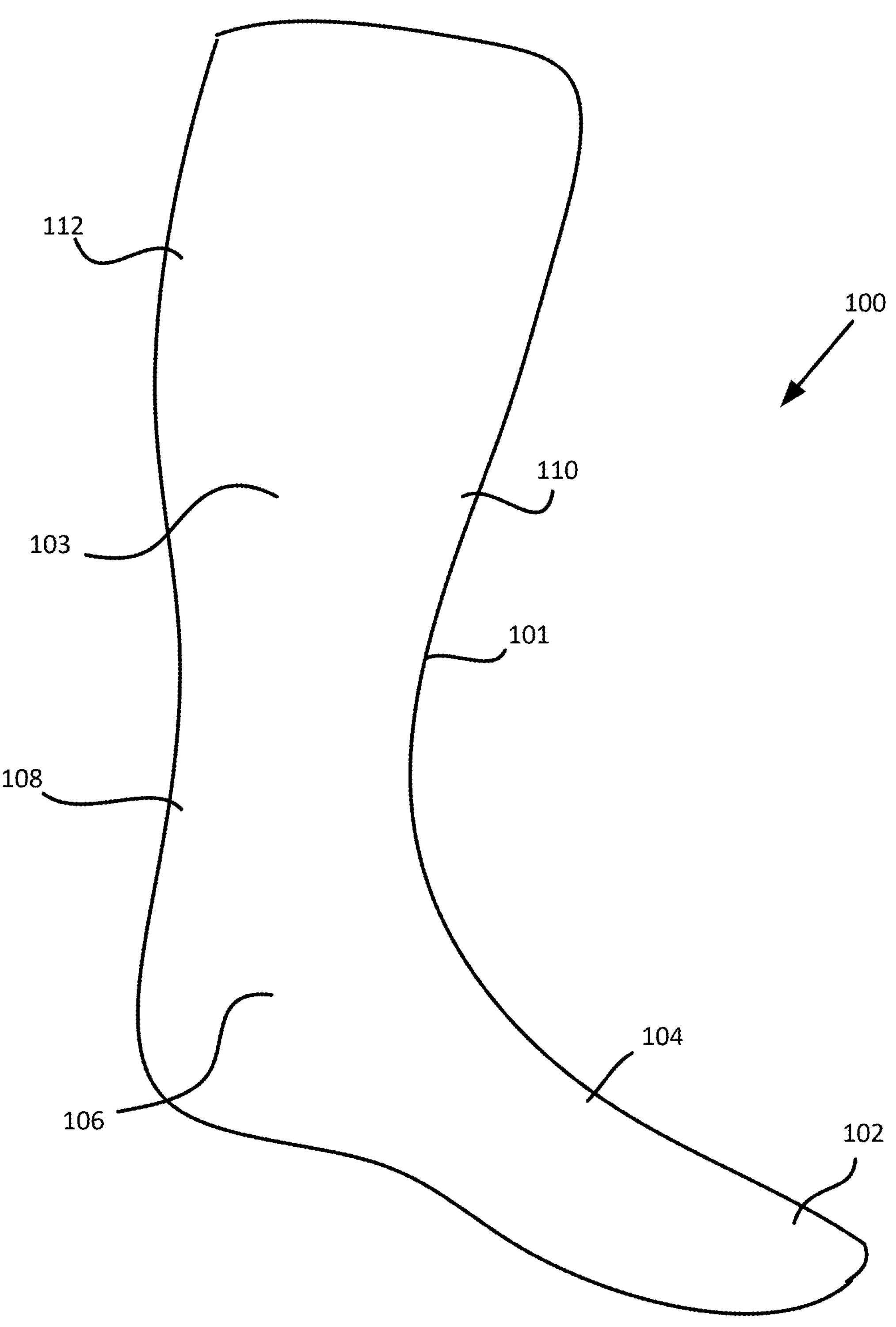
FIG. 1 illustrates a perspective view of a compression sock in accordance with an embodiment of the present disclosure.

FIG. 1 illustrates a perspective view of a compression sock in accordance with an embodiment of the present disclosure. Here, the compression sock 100 is shown in a lightly stretched condition to highlight details of the compression sock 100, as opposed to an unworn condition (e.g., folded in a drawer). It will be understood by those of ordinary skill in the art that compression socks stretch to the shape and contours of a wearer's foot and/or leg, and that none of the figures described herein are intending to illustrate the compression sock 100 as it would appear on the body of ever wearer.

The compression sock 100 of FIG. 1 includes a body 101. The body 101 includes an inner face and an outer face 103. Generally, the inner face may be seen when the sock is turned inside out, given that the inner face is configured to interface with a wearer's anatomy when worn. The body 101 includes a forefoot region 102, a midfoot region 104, a hindfoot region 106, a tendon region 108, a shin region 110, and a calf region 112. These regions correspond to the regions of a typical human limb, the anatomy of which is described in further detail in FIGS. 2-4.

Figure 2:
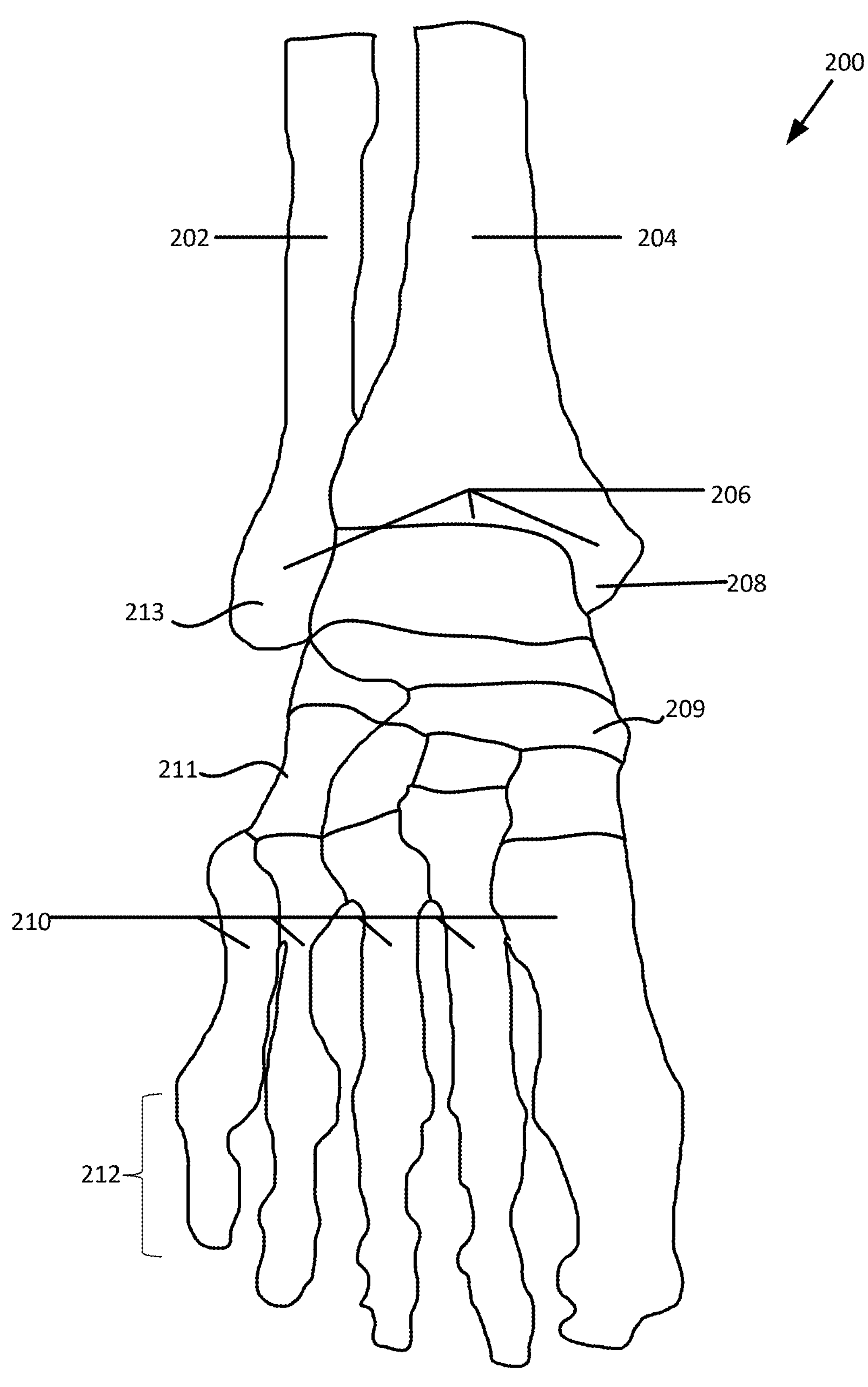
FIG. 2 is a cross-section drawing of the anatomy of a typical human foot, as well as a partial view of a human tibia and fibula.

FIG. 2 is a cross-section drawing of the anatomy of a typical human foot, as well as a partial view of a human tibia and fibula.

As shown, a foot 200 includes a plurality of phalanges 212 and metatarsals 210. Colloquially, the phalanges 212 are the toes or digits of the foot 200. The metatarsals 210 connect the phalanges 212 to the rest of the foot 200, and help form the arches of the foot 200, which are essential in both weight bearing and walking. To do so, the metatarsals are necessarily of prismoid shape. Moreover, the fifth metatarsal (e.g., most proximal the smallest toc) includes a tuberosity portion that appears as a rounded protrusion. This protruding portion of the metatarsal set presents the first challenge to anyone attempting to don a compression sock over the foot 200.

Connected to the metatarsals is the cuboid 211, an irregular cube-like shaped bone which helps provide the foot 200 with stability. Like the fifth metatarsal, the cuboid 211 also includes small bony prominence (tuberosity) that presents a challenge to donning a compression sock. Similarly, next to the cuboid 211 is the medial navicular 209, which connects the ankle to the foot, and is itself an irregular pyriform bone having a large protuberance (another challenge). The medial navicular 209 and cuboid 211 are part of the midfoot.

As shown in FIG. 2, a human's tibia 204 and fibula 202 form an ankle mortise 206, which itself consists of a medial malleolus 208 and lateral malleolus 213. This region is colloquially referred to the as the ankle. The ankle may also be considered part of the hindfoot. The irregular shape of this region, particularly the protruding angles of the medial malleolus 208 and lateral malleolus 213 present additional challenges to donning a compression sock.

Figure 3:
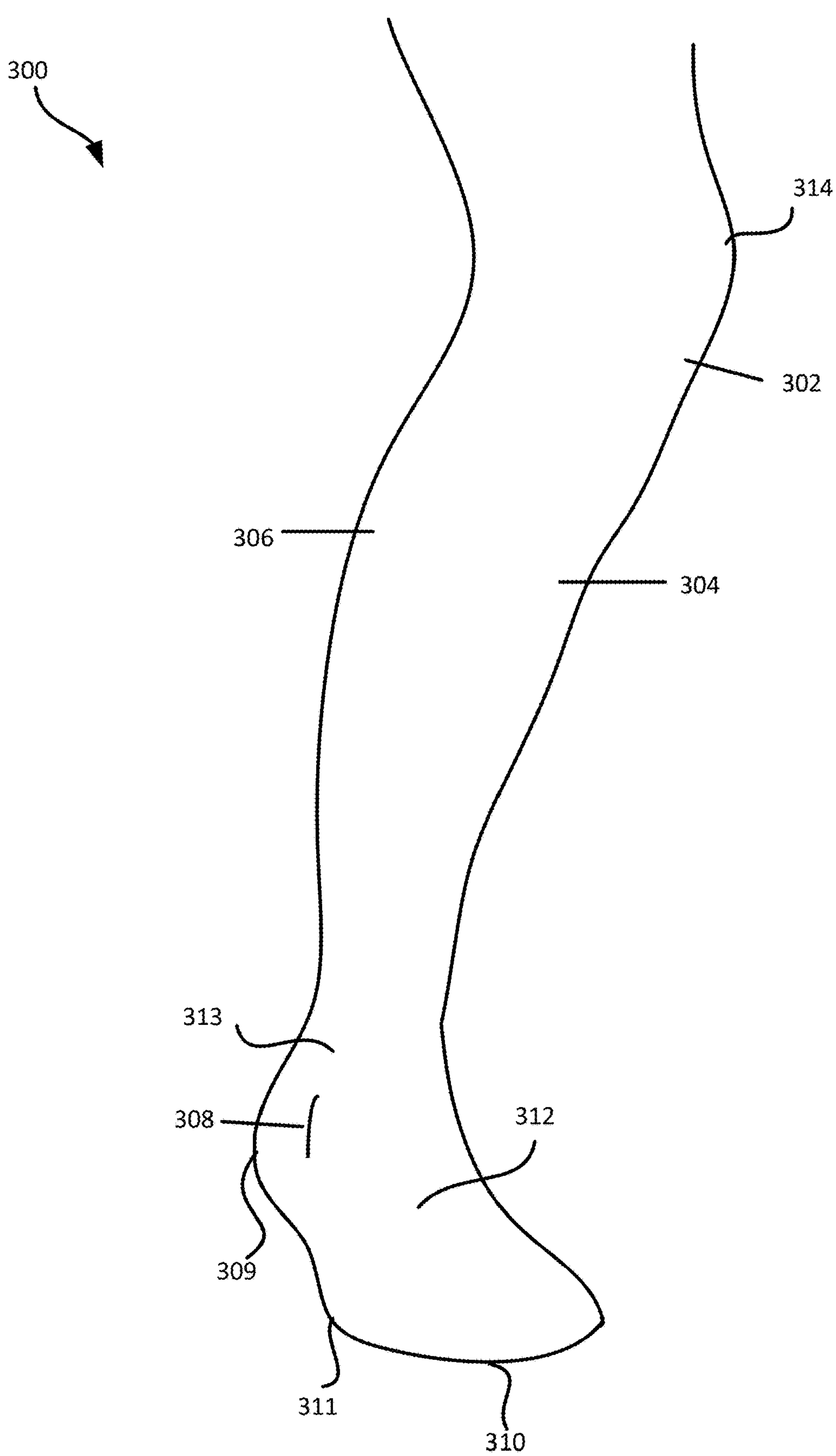
FIG. 3 is a drawing of the anatomy of a typical human leg.
Figure 4:
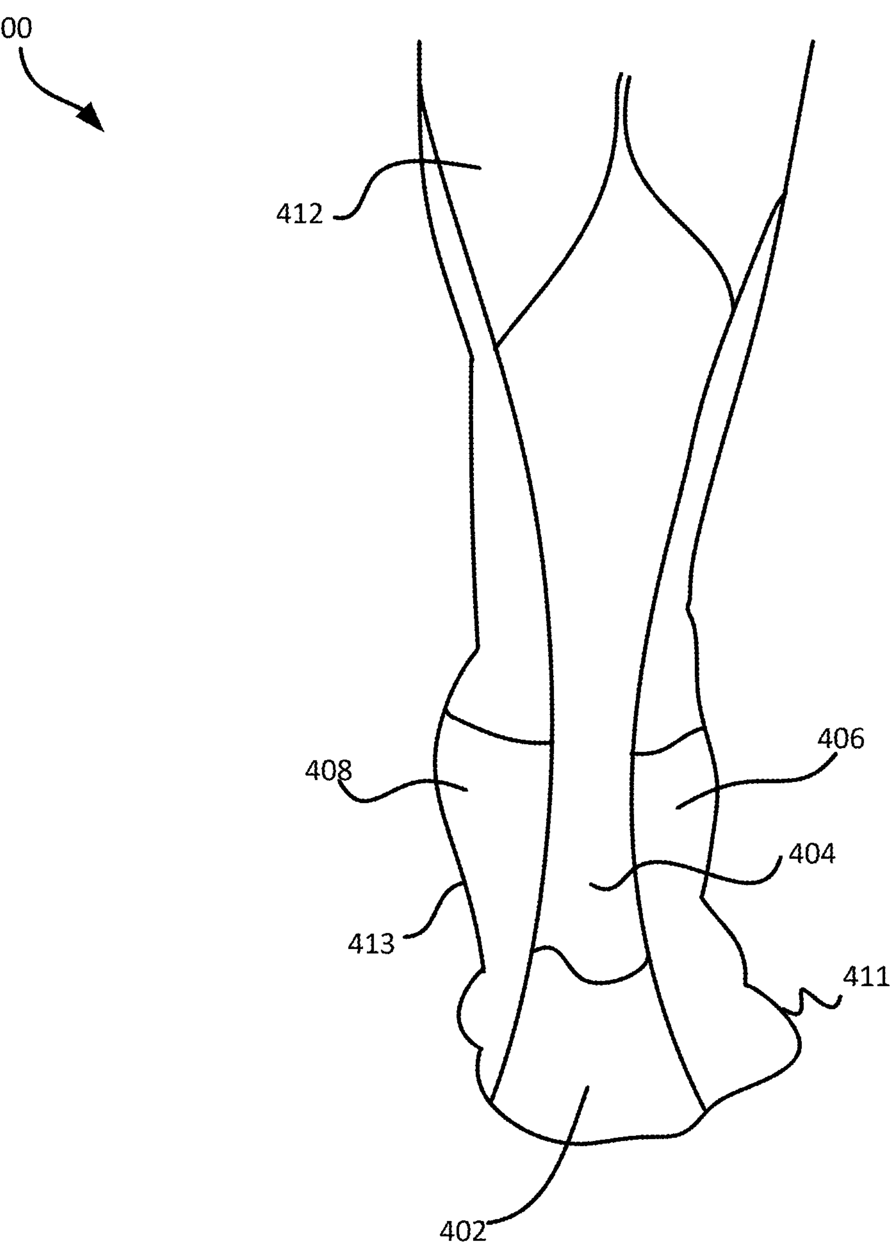
FIG. 4 is a cross-section drawing of the posterior calf and tendon anatomy of a typical human leg.

FIG. 3 is an outline of a typical human leg and FIG. 4 is a cross-section drawing of the posterior calf and tendon anatomy of a typical human leg.

As shown in FIGS. 3 and 4, the leg 300 (400) demonstrates the variety of contours the compression sock (FIG. 1. 100) must accommodate. A forefoot 310, comprised of irregularly shaped toes and joints, is tapered. A tuberosity 311 (411) on the fifth metatarsal protrudes from this tapered shape, angling back into a curve at a midfoot 312. A lateral malleolus 308 (406) and medial malleolus 408 (collectively, the ankle) appear as rounded protrusions at a hindfoot 313 (413). Similarly, a heel 309 (402) rounds out the hindfoot 313 (413). From the heel 309 (402), a compression sock may be pulled up the leg 300 at a substantially 90-degree angle. A tibial region 304 (e.g., shin region) extends from the hindfoot 313 to a tibial tuberosity 302 just below the knee 314.

While the tibial region 304 (e.g., anterior shin) of the leg 300 may appear to be substantially planar, a posterior calf 306 (412) is not. The posterior calf 306 (412) may be slightly curved or significantly arched, depending on the thickness of a wearer's calf muscle.

Likewise, in FIG. 4, the leg 400 includes a tendon connecting the posterior calf muscles to the heel bone, a strong fibrous cord known as the Achilles tendon 404. The Achilles tendon 404 is the thickest tendon in the human body and is responsible for plantar flexion of the foot at the ankle. The Achilles tendon 404 is also irregularly shaped, being thicker at the middle of the calf and gradually thinning as it approaches the heel 402.

Anyone attempting to put on or take off the compression sock (FIG. 1 100) must contend with each of these unique anatomical structures simultaneously. The compression socks described herein may include integrated compression sock aids that optimize the friction between the sock and the wearer's skin at key catch points (unique anatomical structures) of the wearer's leg, such that the compression sock is easy to don while still maintaining compression integrity after donning. As described herein, the compression sock fabric in contact with the wearer's skin may be released with enough force at key anatomical structures, enabling the rest of the sock to slide on easily. For example, the fabric may be released on the sagittal plane (mid-line) of the heal and ankle. In such embodiments, the pulls, grips, and/or openings, described herein, may be more effective when located at anterior and posterior anatomical regions than at medial and lateral anatomical regions. The more such pulls, grips, and/or openings release the fabric at a centerline of the heel/ankle, the easier the compression sock is to don.

Figure 5:
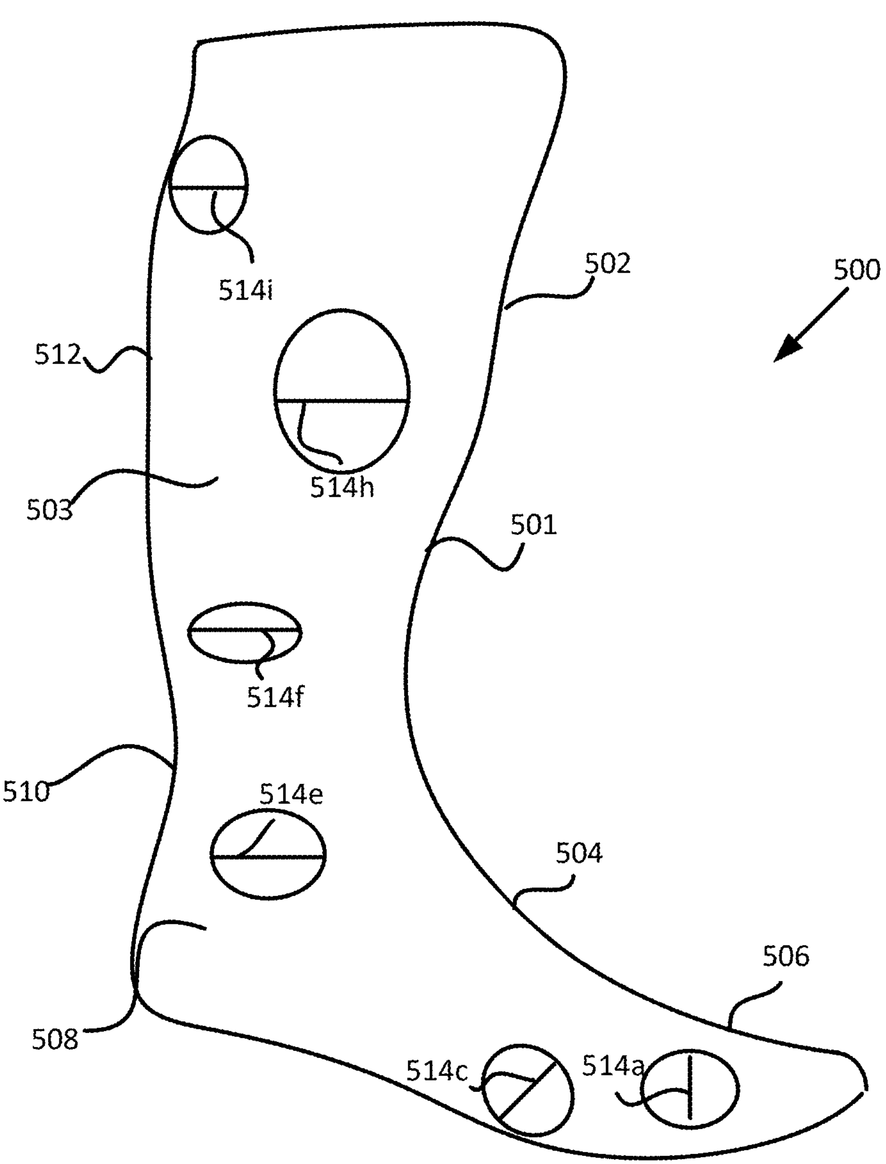
FIG. 5 is a perspective view of a compression sock in accordance with an embodiment of the present disclosure.
Figure 6:
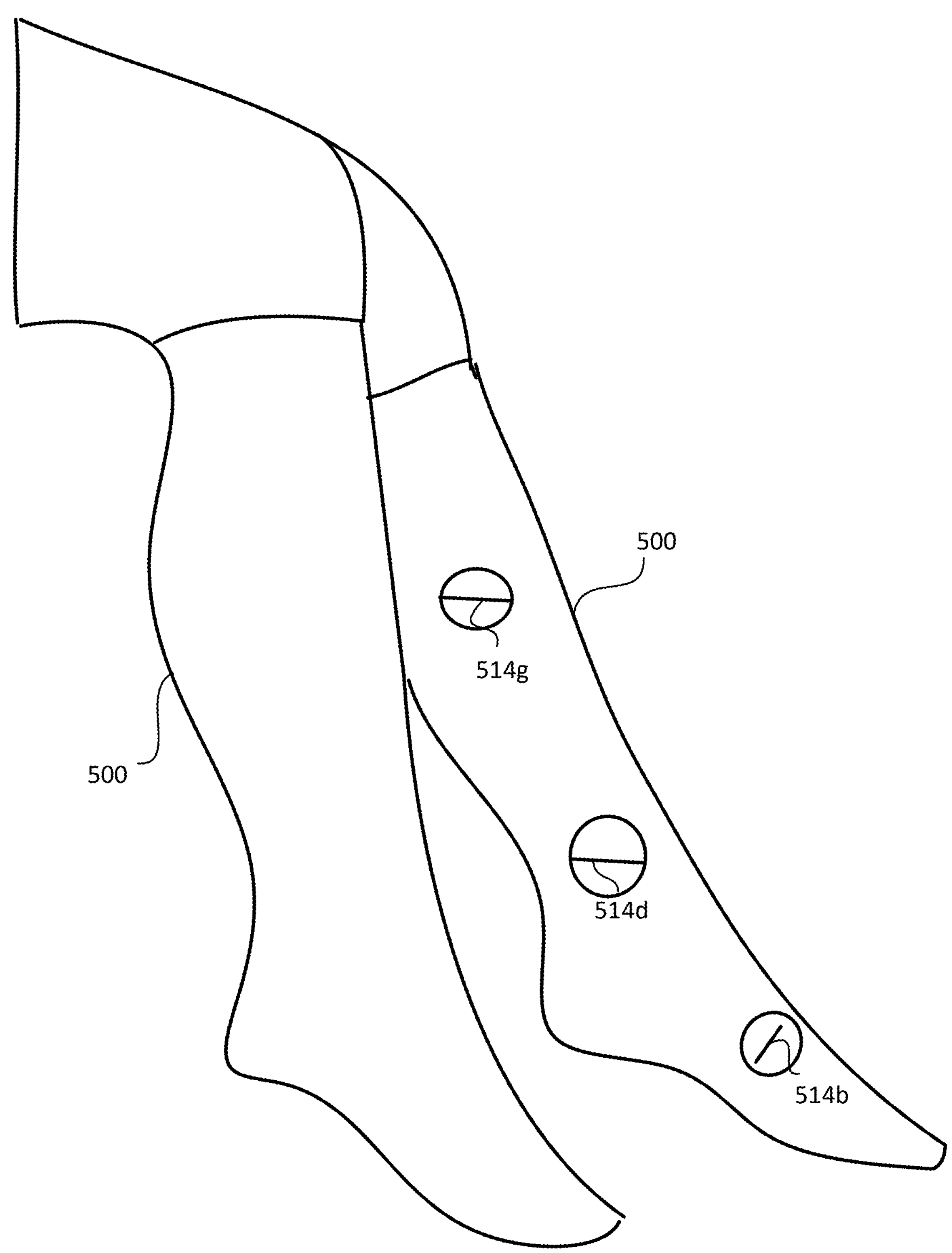
FIG. 6 is a perspective view of the compression sock of FIG. 5, as worn on both legs.

FIG. 5 is a perspective view of a compression sock in accordance with an embodiment of the present disclosure. Moreover, FIG. 6 is a perspective view of the compression sock of FIG. 5, as worn on both legs.

The wearer may be a patient afflicted with venous reflux resulting in lower leg swelling, skin changes and ulcerations. The wearer may be a user attempting to improve symptoms and mobility associated with venous disorders such as edema, phlebitis, and thrombosis. The wearer may be an athlete or user engaged in athletic activities, or a preventative care everyday user, or any user attempting to improve blood flow throughout the lower extremities. Accordingly, a compression sock 500 may have a strength ranging from 10-20 mm/Hg, 20-30 mm/Hg, 30-40 mm/Hg, and/or 40-50 mm/Hg.

The body 501 includes an inner face and an outer face 503. Generally, the inner face may be seen when the sock is turned inside out, given that the inner face is configured to interface with a wearer's anatomy when worn. Accordingly, the inner face may be a smooth uninterrupted surface configured to minimize irritation of the skin.

The plurality of sequential pulls may be a system to aid wearers (and those assisting them) in donning and doffing the compression sock 500. As shown in the present embodiment of FIGS. 5 and 6, there are first through ninth sequential pulls 514*a-i.*

In various embodiments, the plurality of sequential pulls 514*a-i* may be coupled to the outer face 503. In various embodiments, the plurality of sequential pulls 514*a-i* may be optionally coupled to any part of the outer face 503. The plurality of sequential pulls 514*a-i* may be stitched, glued, tied, stuck, strapped, bound, clipped, grafted onto, or otherwise attached to the outer face 503. In various embodiments, the plurality of sequential pulls 514*a-i* may be in either a substantially vertical or substantially horizontal orientation relative the compression sock 500. In various aspects, the plurality of sequential pulls 514*a-i* may be cut into the outer face 503 and reinforced with stitching reinforcement or additional material around the incisions to form the pulls 514*a-i*. Stitching reinforcement or additional material may be, for example, two overlying pieces of neoprene or low friction fabric. For example, the two overlaying pieces of neoprene or low friction fabric may be stitched on either side (a proximal side and a distal side) of each of the plurality of sequential pulls 514*a-i*. In various embodiments, the proximal side may be a top side and the distal side may be a bottom side, with the neoprene or low friction fabric of the proximal side overlaying the neoprene or low friction fabric of the distal side.

In various embodiments, the plurality of sequential pulls 514*a-i* may be integrated into the outer face 503 by, for example, three-dimensional (3D) manufacturing techniques. In various embodiments, each of the plurality of sequential pulls 514*a-i* may be large enough to accommodate one or two fingers, or an aid hook, but small enough to avoid fabric bunching under footwear or clothing. In various embodiments, each of the plurality of sequential pulls 514*a-i* may range in width between 0.1 inches (in)-0.5 in, 0.5 in-0.75 in, 0.75 in-1 in, 1 in-2 in, or 2-3 in wide. In various embodiments, each of the plurality of sequential pulls 514*a-i* may range in thickness between 0.01 inches (in)-0.05 in, 0.05 in-0.10 in, 0.10 in-0.15 in, 0.15 in-0.2 in, 0.2 in-0.25 in, 0.25 in-0.3 in, or 0.3 in-0.5 in thick. In various embodiments, each of the plurality of sequential pulls 514*a-i* may be 0.25 in thick. In various embodiments, the stitching reinforcement or additional material may range in width between 0.1 inches (in)-0.5 in, 0.5 in-0.75 in, 0.75 in-1 in, 1 in-2 in, or 2-3 in wide. In various embodiments, the stitching reinforcement or additional material may be 0.25 in wide.

In various embodiments, the plurality of sequential pulls 514*a-i* may be placed along the body 501 of the compression sock 500 where the pulls 514*a-i* will create the most leverage (e.g., mechanical advantage) for the wearer, assistant, or an aid to pull the sock on and take the sock off (e.g., donning and doffing).

For instance, the body 501 includes a forefoot region 506, a midfoot region 504, a hindfoot region 508, a tendon region 510, a shin region 502, and a calf region 512. These regions correspond to regions of a typical human limb, the anatomy of which was described above in reference to FIGS. 2-4.

Each region is located proximal to at least one pull of the plurality of sequential pulls 514*a-i*. For example, in various embodiments, the forefoot region 506 of the body 501 is proximal a wearer's metatarsals. The midfoot region 504 is proximal a wearer's medial navicular and lateral cuboid. The hindfoot region 508 is proximal a wearer's medial malleolus, lateral malleolus, and heel. The tendon region 510 is proximal a wearer's Achilles tendon. The shin region 502 is proximal a wearer's medial tibial tuberosity and lateral tibial tuberosity. The calf region 512 is proximal a wearer's posterior calf.

As shown in FIGS. 5 and 6, a first pull 514*a* is proximal the forefoot region 506. The first pull 514*a* may therefore generate leverage in donning and doffing the compression sock 500 over the wearer's metatarsals. This first pull 514*a* is also useful given that the forefoot region 506 is harder to grasp due to sock bunching that might occur at the wearer's phalanges and metatarsals. A second pull 514*b* is proximal the midfoot region 504 and specifically proximal the wearer's medial navicular, generating leverage in donning and doffing the compression sock 500 over the wearer's medial navicular. A third pull 514*c* is also proximal the midfoot region 504, and specifically proximal the wearer's lateral cuboid, generating leverage in donning and doffing the compression sock 500 over the wearer's lateral cuboid.

Likewise, a fourth pull 514*d* is proximal the hindfoot region 508 and wearer's medial malleolus, generating leverage in donning and doffing the compression sock 500 over the wearer's medial malleolus. A fifth pull 514*e* is also located proximal the hindfoot region 508, and specifically proximate the wearer's lateral malleolus. The fifth pull 514*e* may generate leverage in donning and doffing the compression sock 500 over the wearer's lateral malleolus. Being on either side of the ankle, the fourth pull 514*d* and fifth pull 514*e* are also proximate the heel, and together or on their own, may generate leverage in donning and doffing the compression sock 500 over the wearer's heel. Using both the fourth pull 514*d* and fifth pull 514*e* to generate leverage over the heel may be advantageous given that the heel represents the sharpest angular turn as the sock is pulled up the leg.

Similarly, a sixth pull 514*f* is located proximal the tendon region 510 and may generate leverage in donning and doffing the compression sock 500 over the wearer's Achilles tendon. A seventh pull 514*g* is located proximal the shin region 502 and wearer's medial tibial tuberosity and may generate leverage in donning and doffing the compression sock 500 over the wearer's medial tibial tuberosity. Similarly, an eighth pull 514*h* is also located proximal the shin region 502, and specifically, the wearer's lateral tibial tuberosity, and may generate leverage in donning and doffing the compression sock 500 over the wearer's lateral tibial tuberosity.

Moreover, as shown, a ninth pull 514*i* is located proximal the calf region 512 and may generate leverage in donning and doffing the compression sock 500 over the wearer's posterior calf.

Accordingly, as the wearer, assistant, or aid is pulling the sock 500 over the wearer's leg, the pulls 514*a-i* may be manipulated in sequential order, thus generating sufficient leverage to pull the compression sock 500 over parts of the anatomy that challenge those with limited mobility and/or grip strength.

In various embodiments, the compression sock 500 may be made of any suitable compressive fabric, including elastane, cotton, microfiber, and the like, and composites thereof. In various embodiments, the plurality of sequential pulls 514*a-i* may be made of a fabric such as polyester, nylon, elastane, and the like, and composites thereof, or any fabric suitable for the pulls to stretch to lay flat when not in use.

Figure 7:
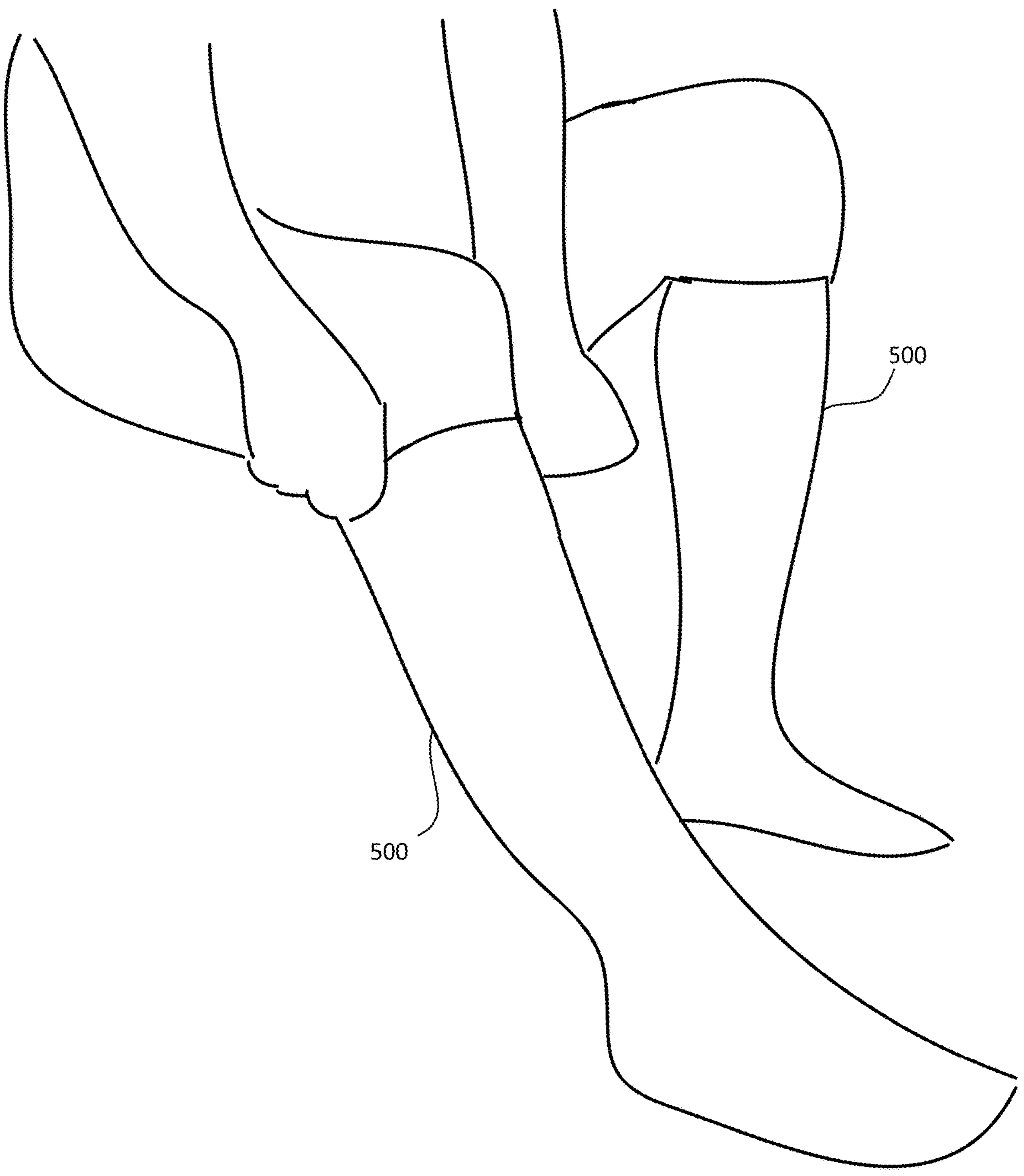
FIG. 7 is a perspective view of the compression sock of FIGS. 5 and 6, as worn on both legs.
Figure 8:
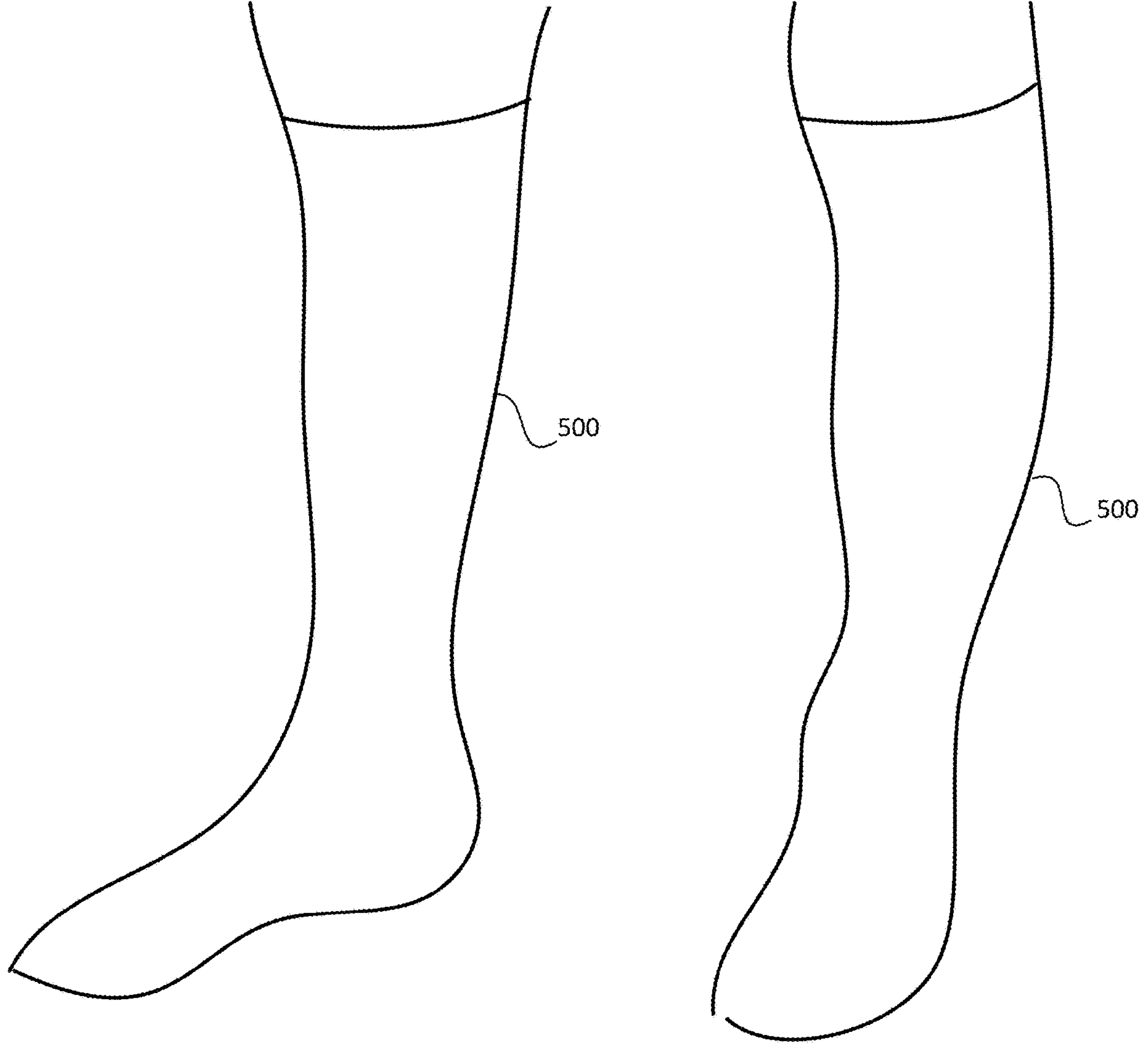
FIG. 8 is a perspective view of the compression sock of FIGS. 5-7, as worn on both legs.
Figure 9:
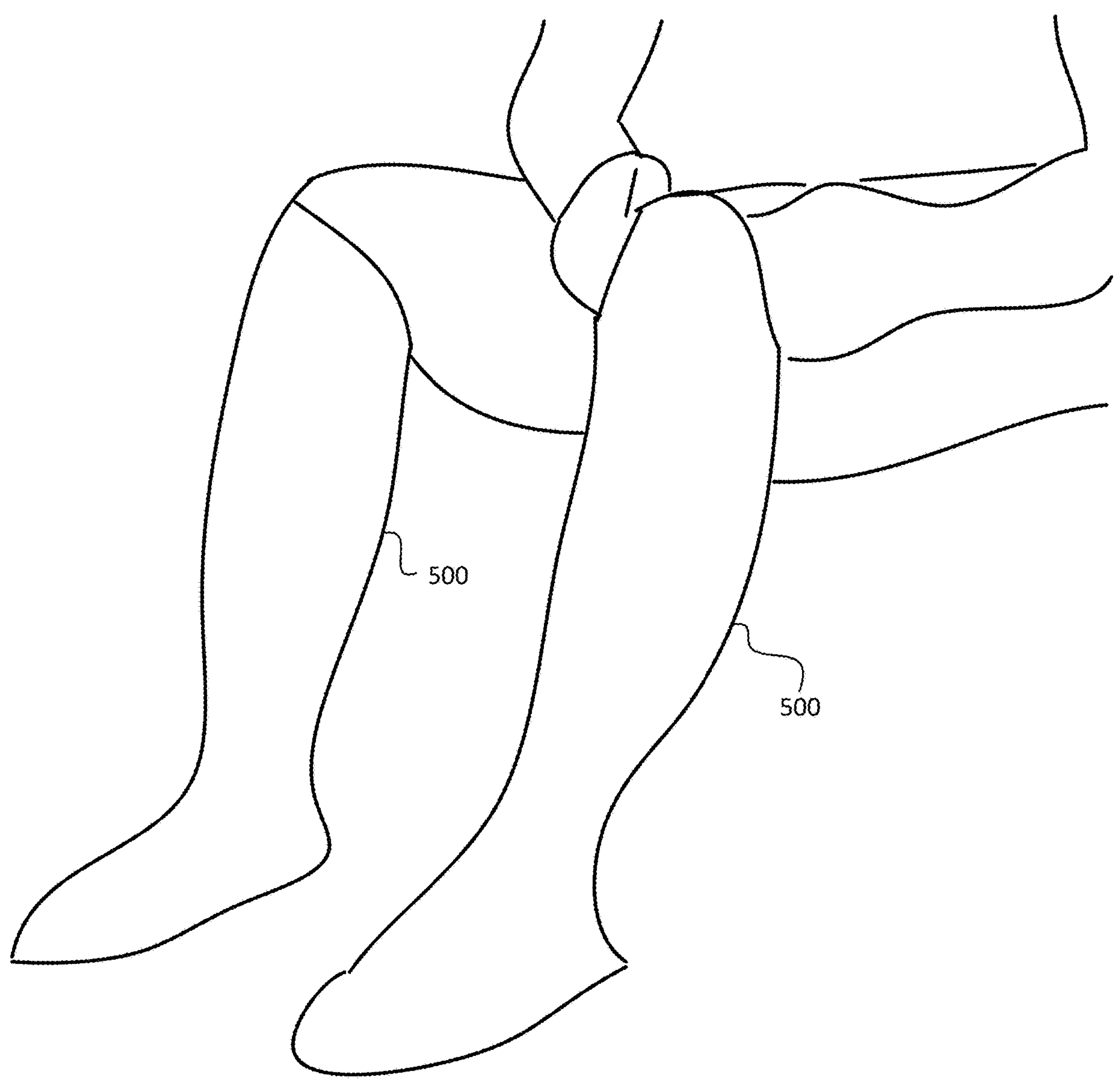
FIG. 9 is a perspective view of the compression sock of FIGS. 5-8, as worn on both legs.

FIGS. 7 through 9 are each additional perspective views of the compression sock 500 of FIGS. 5 and 6, as worn on both legs.

Figure 10:
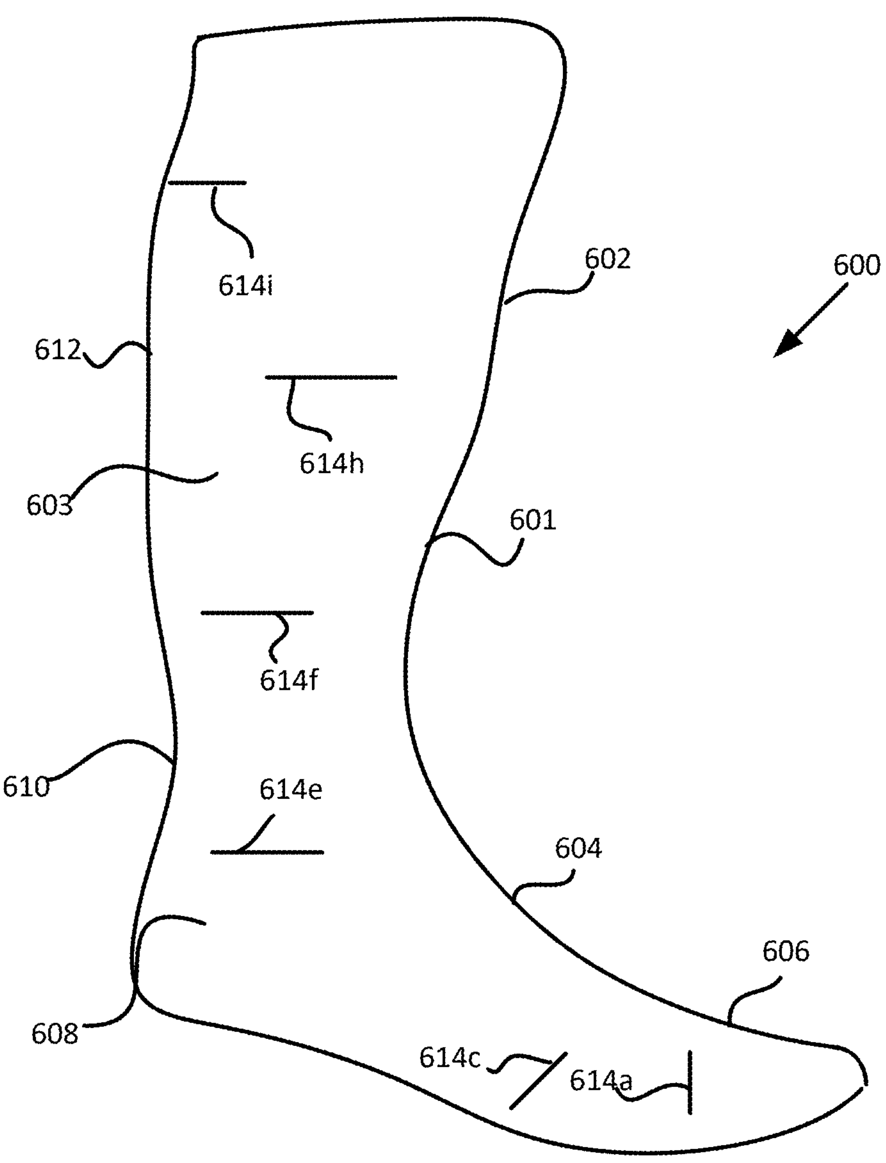
FIG. 10 is a perspective view of a compression sock in accordance with an embodiment of the present disclosure.
Figure 11:
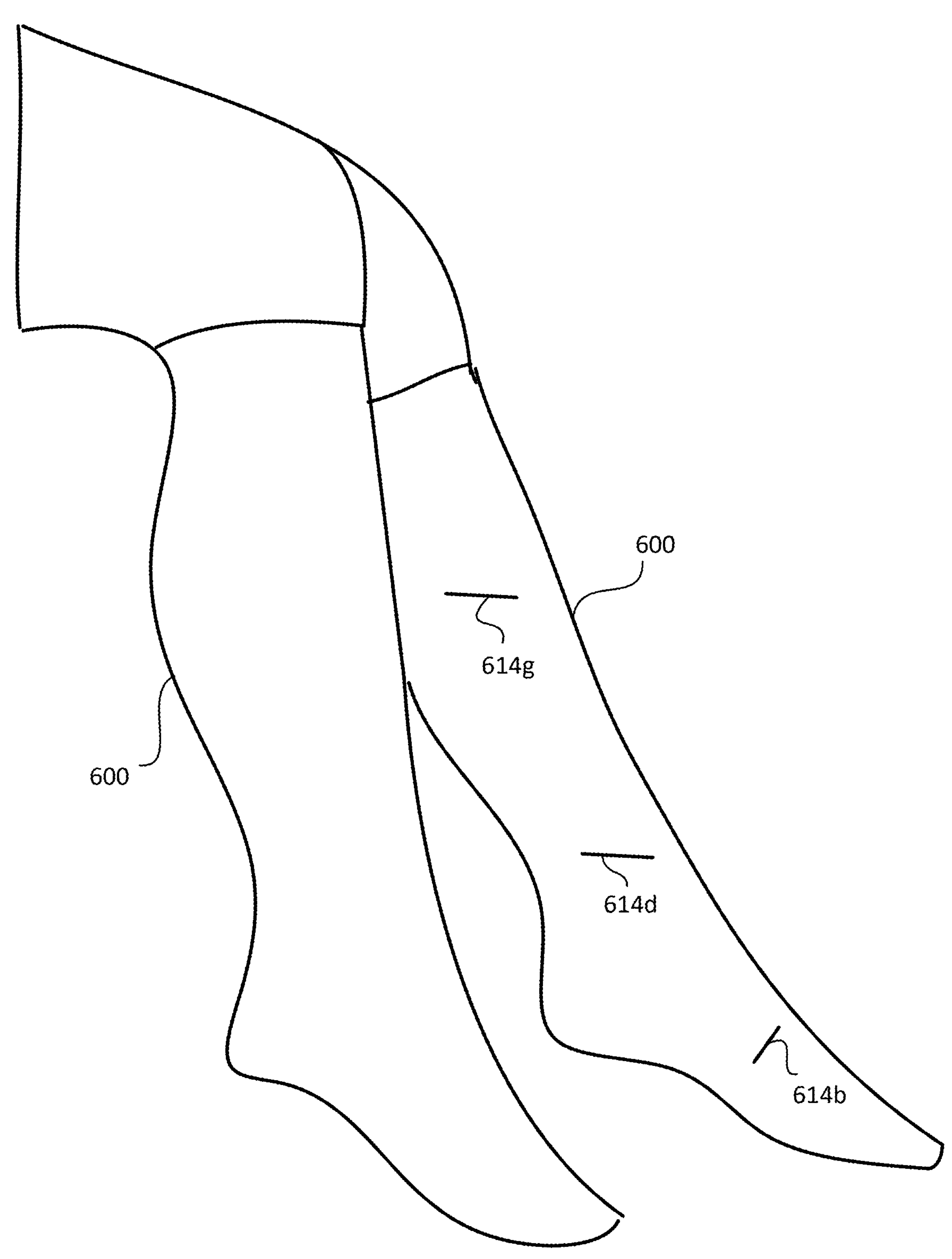
FIG. 11 is a perspective view of the compression sock of FIG. 10, as worn on both legs.

FIG. 10 is a perspective view of a compression sock in accordance with an embodiment of the present disclosure. Moreover, FIG. 11 is a perspective view of the compression sock of FIG. 10, as worn on both legs.

The wearer may be a patient afflicted with venous reflux resulting in lower leg swelling, skin changes and ulcerations. The wearer may be a user attempting to improve symptoms and mobility associated with venous disorders such as edema, phlebitis, and thrombosis. The wearer may be an athlete or user engaged in athletic activities, or a preventative care everyday user, or any user attempting to improve blood flow throughout the lower extremities. Accordingly, a compression sock 600 may have a strength ranging from 10-20 mm/Hg, 20-30 mm/Hg, 30-40 mm/Hg, and/or 40-50 mm/Hg.

The compression sock 600 may include a body 601 defining first through $n^{th}$ sequential openings (e.g., plurality of sequential openings). The compression sock 600 may include a body 601 defining any number of sequential openings. The body 601 includes an inner face and an outer face 603. Generally, the inner face may be seen when the sock is turned inside out, given that the inner face is configured to interface with a wearer's anatomy when worn. Accordingly, the inner face may be a smooth uninterrupted surface configured to minimize irritation of the skin.

In embodiments, the number of sequential openings is limited, as shown in FIG. 10, so that openings are only provided over or adjacent to specific regions of the leg when compression sock 600 is worn. For example, the openings may only be provided over or adjacent to forefoot region 606, midfoot region 604, hindfoot region 608, tendon region 610, shin region 602, and calf region 612. This effectively limits the number of openings that may be formed, thereby limiting their placement to specific regions of the leg. If, for example, a large number of openings were to be placed all over compression 600, that could be problematic for the wearer.

Specifically, the locations of the openings for compression sock 600 are dictated by both anatomical necessity as well as physics to maximally reduce the force required to don the compression sock 600. The Law of Laplace dictates that the garment will be tightest over the narrowest anatomical areas, as expressed by the equation P=T/r, where P=Pressure exerted on the surface, T=Tension in the garment, and r=Radius of the curvature of the area being compressed.

Therefore, placing the openings as illustrated in FIG. 10 to release these areas significantly reduces the forces required to pull the garment into the proper position. The number of openings should be so limited so as to maintain the compression function of compression sock 600 (too many, or arbitrarily-placed openings would greatly weaken the compression sock, effectively rendering it unable to perform its function) and physical integrity-care must be taken to interrupt the textile of compression sock 600 as little as possible. Any additional openings will directly compromise the overall strength of compression sock 600, increasing the likelihood that it will rip.

The use of too many openings (e.g., openings formed in locations that don't play a role in assisting in the donning or removal of compression sock 600) will negatively affect the compressive capabilities of compression sock 600. Additionally, an overabundance of access openings may lead to blistering to the skin. As noted in Moffatt, C. J., O'Hare, L., & Mercier, G. (2020). Risks and Contraindications of Medical Compression Treatment. *Phlebology,* 35(4), 235-244, the skin moves differently in areas with different compression. This differential causes shear forces between the different areas and can lead to edema and significant blistering.

The plurality of sequential openings may be a system to aid wearers (and those assisting them) in donning and doffing the compression sock 600. As shown in the present embodiment of FIGS. 10 and 11, there are first through ninth sequential openings 614*a-i*.

In various embodiments, the outer face 603 may define the plurality of sequential openings 614*a-i*. In various embodiments, the outer face 603 may optionally define the plurality of sequential openings 614*a-i* at any part of the outer face 603. In various embodiments, the plurality of sequential openings 614*a-i* may be in either a substantially vertical or substantially horizontal orientation relative the compression sock 600. In various aspects, the plurality of sequential openings 614*a-i* may be cut into the outer face 603. In various aspects, the plurality of sequential openings 614*a*-I may be reinforced with stitching around the incisions that form the openings 614*a-i*. In various embodiments, each of the plurality of sequential openings 614*a-i* may be large enough to accommodate one or two fingers, or an aid hook, but small enough to avoid fabric bunching under footwear or clothing. In various embodiments, each of the plurality of sequential openings 614*a-i* may range in width between 0.1 inches (in)-0.5 in, 0.5 in-0.75 in, 0.75 in-1 in, 1 in-2 in, or 2-3 in wide. In various embodiments, each of the plurality of sequential openings 614*a-i* may be 0.75 in wide.

In various embodiments, the plurality of sequential openings 614*a-i* may be placed along the body 601 of the compression sock 600 where the openings 614*a-i* will create the most leverage (e.g., mechanical advantage) for the wearer, assistant, or an aid to pull the sock on and take the sock off (e.g., donning and doffing).

For instance, the body 601 includes a forefoot region 606, a midfoot region 604, a hindfoot region 608, a tendon region 610, a shin region 602, and a calf region 612. These regions correspond to regions of a typical human limb, the anatomy of which was described above in reference to FIGS. 2-4.

Each region is located proximal to at least one pull of the plurality of sequential openings 614*a-i*. For example, in various embodiments, the forefoot region 606 of the body 601 is proximal a wearer's metatarsals. The midfoot region 604 is proximal a wearer's medial navicular and lateral cuboid. The hindfoot region 608 is proximal a wearer's medial malleolus, lateral malleolus, and heel. The tendon region 610 is proximal a wearer's Achilles tendon. The shin region 602 is proximal a wearer's medial tibial tuberosity and lateral tibial tuberosity. The calf region 612 is proximal a wearer's posterior calf.

As shown in FIGS. 10 and 11, a first opening 614*a* is proximal the forefoot region 606. The first opening 614*a* may therefore generate leverage in donning and doffing the compression sock 600 over the wearer's metatarsals. This first opening 614*a* is also useful given that the forefoot region 606 is harder to grasp due to sock bunching that might occur at the wearer's phalanges and metatarsals. A second opening 614*b* is proximal the midfoot region 604 and specifically proximal the wearer's medial navicular, generating leverage in donning and doffing the compression sock 600 over the wearer's medial navicular. A third opening 614*c* is also proximal the midfoot region 604, and specifically proximal the wearer's lateral cuboid, generating leverage in donning and doffing the compression sock 600 over the wearer's lateral cuboid.

Likewise, a fourth opening 614*d* is proximal the hindfoot region 508 and wearer's medial malleolus, generating leverage in donning and doffing the compression sock 600 over the wearer's medial malleolus. A fifth opening 614*e* is also located proximal the hindfoot region 608, and specifically proximate the wearer's lateral malleolus. The fifth opening 614*e* may generate leverage in donning and doffing the compression sock 600 over the wearer's lateral malleolus. Being on either side of the ankle, the fourth opening 614*d* and fifth opening 614*e* are also proximate the heel, and together or on their own, may generate leverage in donning and doffing the compression sock 600 over the wearer's heel. Using both the fourth opening 614*d* and fifth opening 614*e* to generate leverage over the heel may be advantageous given that the heel represents the sharpest angular turn as the sock is pulled up the leg.

Similarly, a sixth opening 614*f* is located proximal the tendon region 610 and may generate leverage in donning and doffing the compression sock 600 over the wearer's Achilles tendon. A seventh opening 614*g* is located proximal the shin region 602 and wearer's medial tibial tuberosity and may generate leverage in donning and doffing the compression sock 600 over the wearer's medial tibial tuberosity. Similarly, an eighth opening 614*h* is also located proximal the shin region 602, and specifically, the wearer's lateral tibial tuberosity, and may generate leverage in donning and doffing the compression sock 600 over the wearer's lateral tibial tuberosity.

Moreover, as shown, a ninth opening 614*i* is located proximal the calf region 612 and may generate leverage in donning and doffing the compression sock 600 over the wearer's posterior calf.

Accordingly, as the wearer, assistant, or aid is pulling the sock 600 over the wearer's leg, the openings 614*a-i* may be manipulated in sequential order, thus generating sufficient leverage to pull the compression sock 600 over parts of the anatomy that challenge those with limited mobility and/or grip strength.

In various embodiments, the compression sock 600 may be made of any suitable compressive fabric, including elastane, cotton, microfiber, and the like, and composites thereof. In various embodiments, the stitching reinforcing the plurality of sequential openings 614*a-i* may be made of a fabric such as polyester, nylon, elastane, and the like, and composites thereof.

Figure 23:
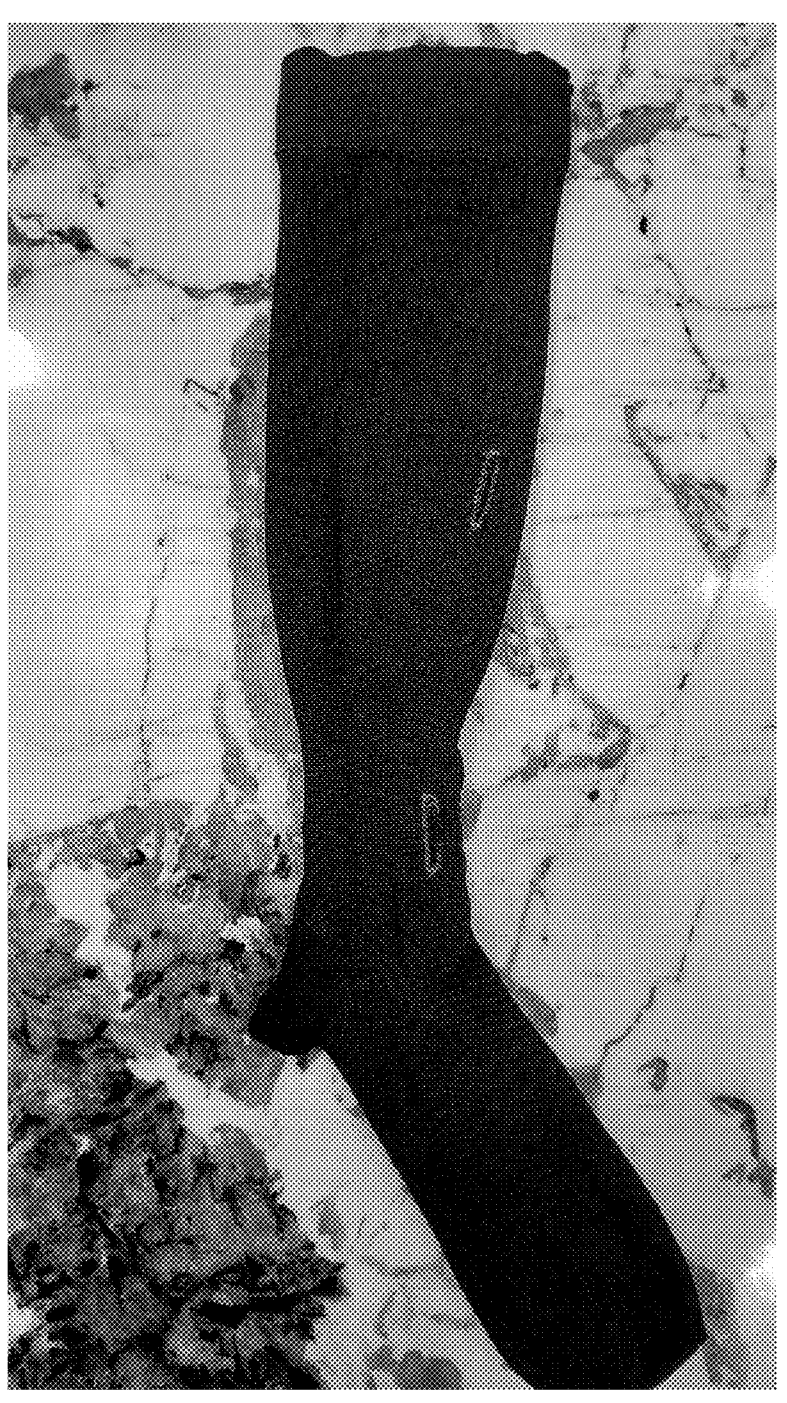
FIGS. 23 and 24 are illustrations of a compression sock incorporating a sequential set of pulls configured as reinforced openings in the compression sock material.
Figure 24:

Openings 614*a-i* may, in some embodiments, be reinforced openings to improve the structural integrity of compression sock 600. To illustrated, FIGS. 23 and 24 are illustrations of a compression sock incorporating a sequential set of pulls configured as reinforced openings in the compression sock material.

Figure 12:
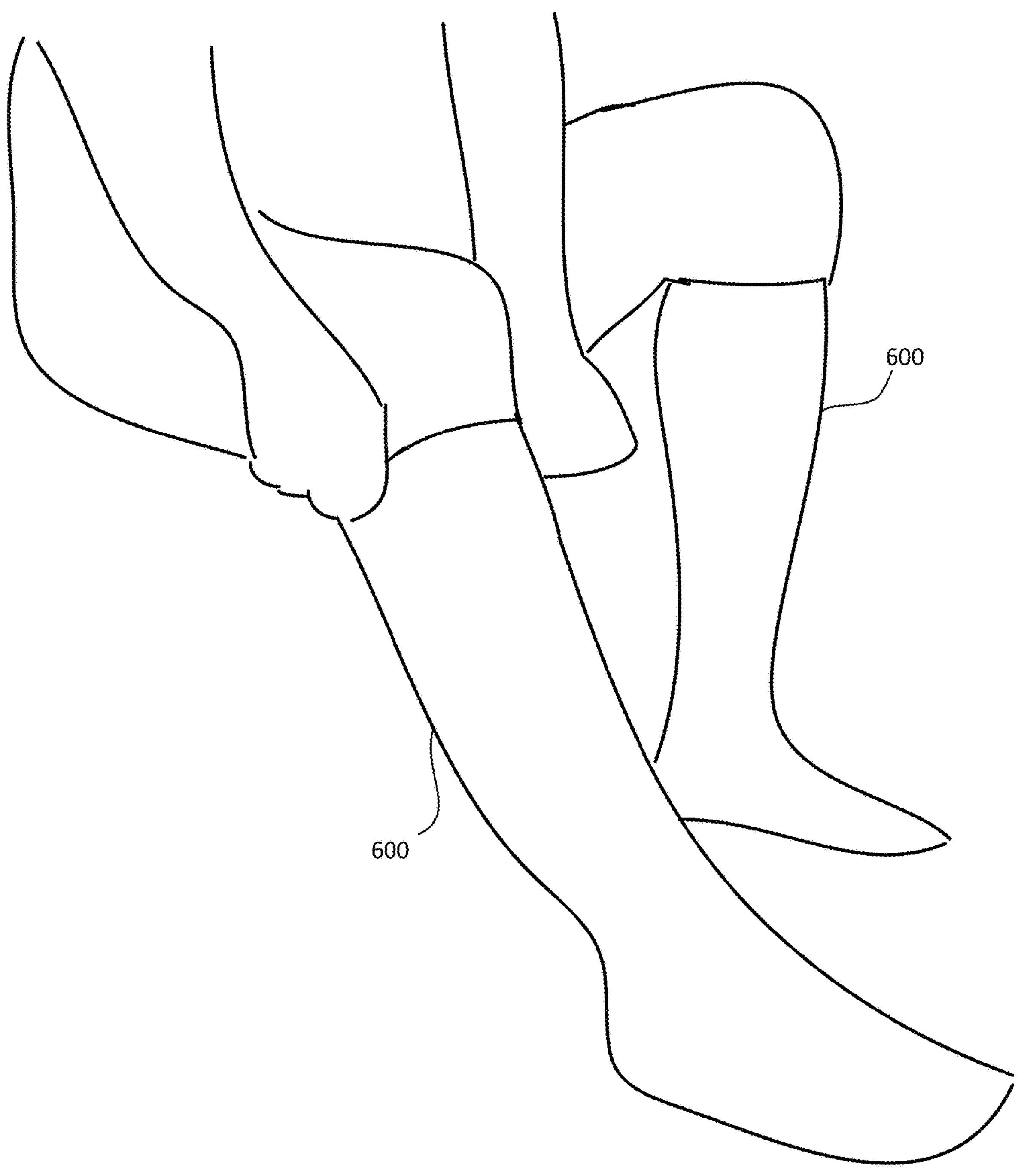
FIG. 12 is a perspective view of the compression sock of FIGS. 10 and 11, as worn on both legs.
Figure 13:
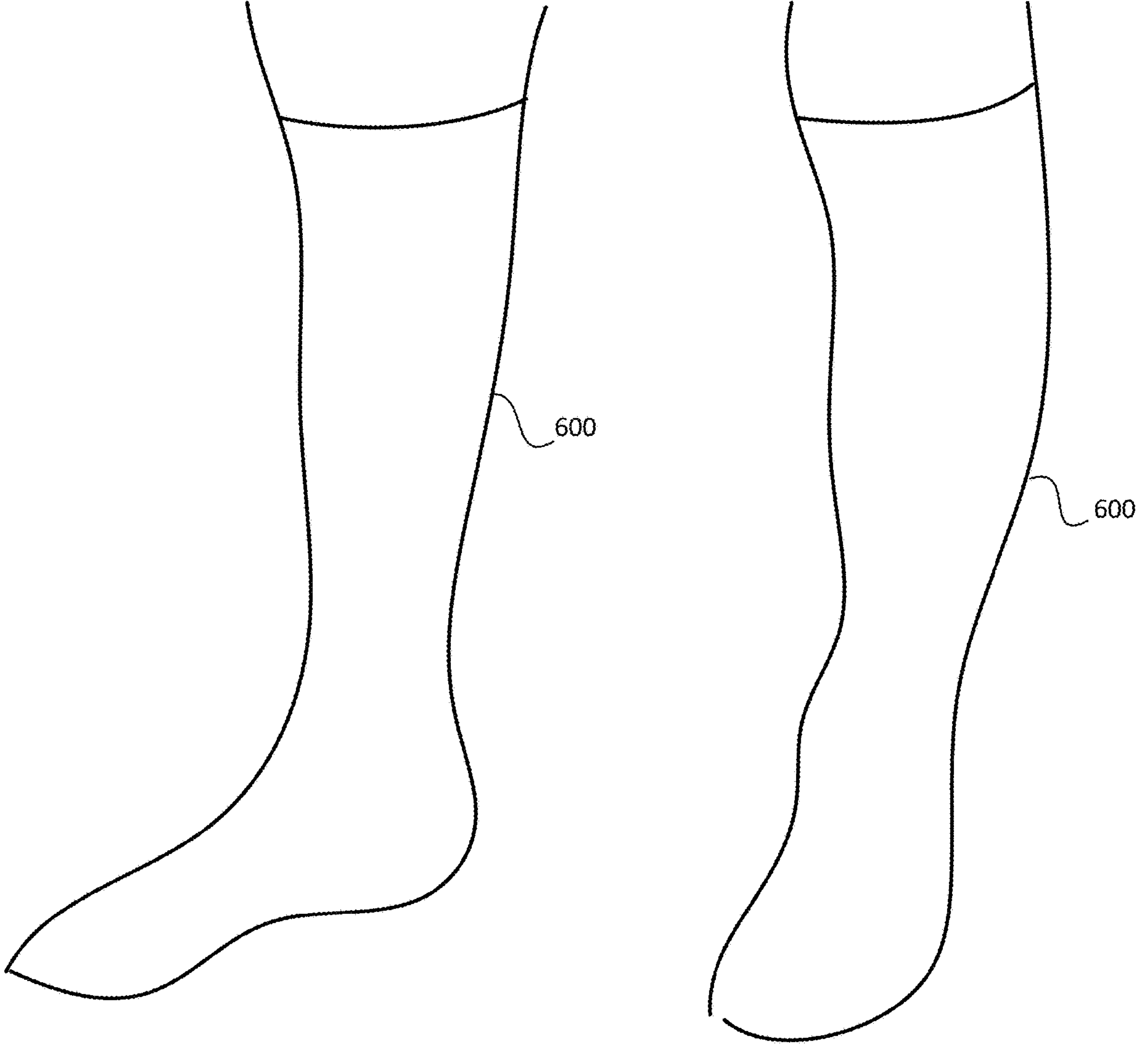
FIG. 13 is a perspective view of the compression sock of FIGS. 10-12, as worn on both legs.
Figure 14:
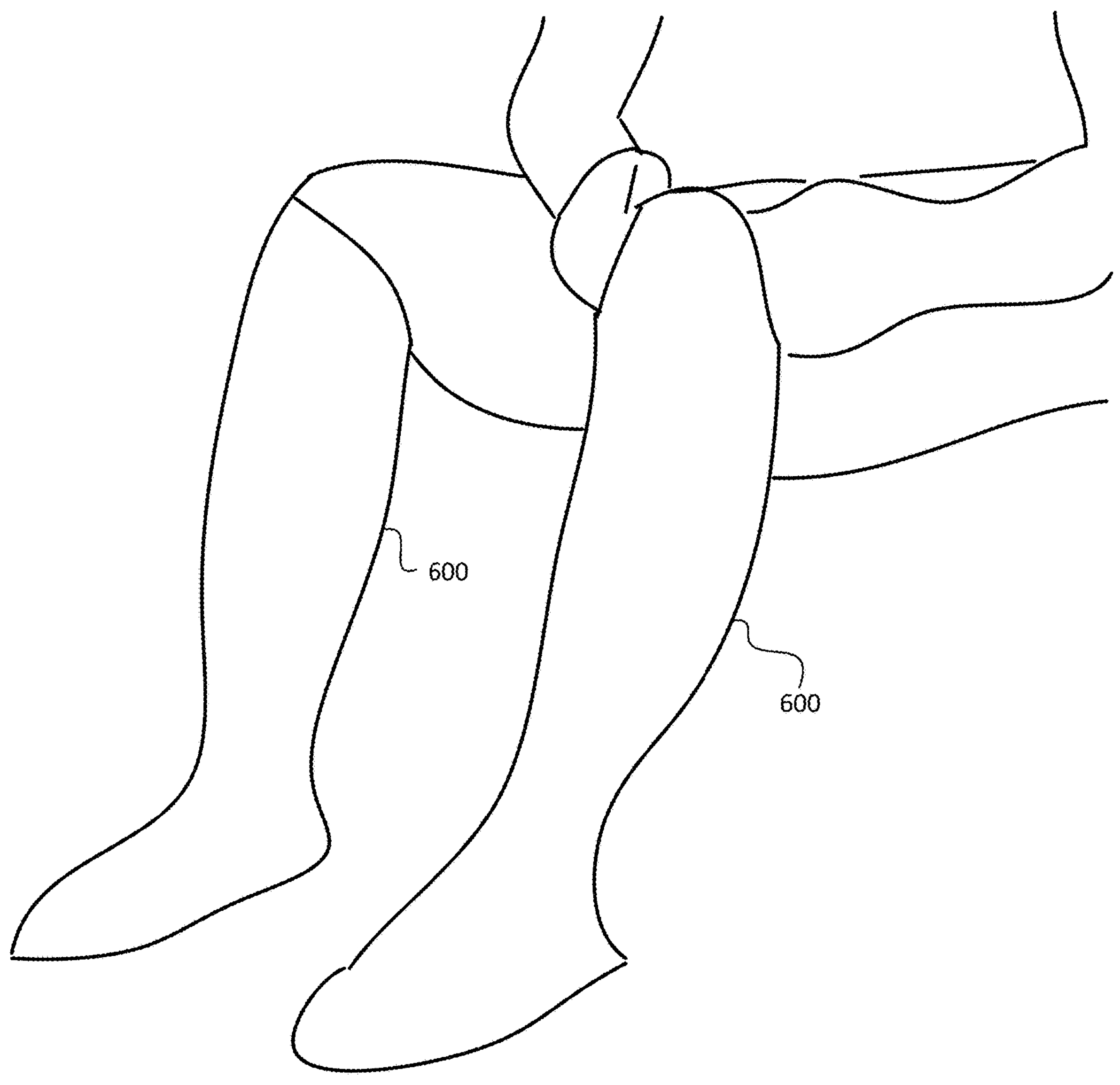
FIG. 14 is a perspective view of the compression sock of FIGS. 10-13, as worn on both legs.

FIGS. 12 through 14 are each additional perspective views of the compression sock 600 of FIGS. 10 and 11, as worn on both legs.

Figure 15:
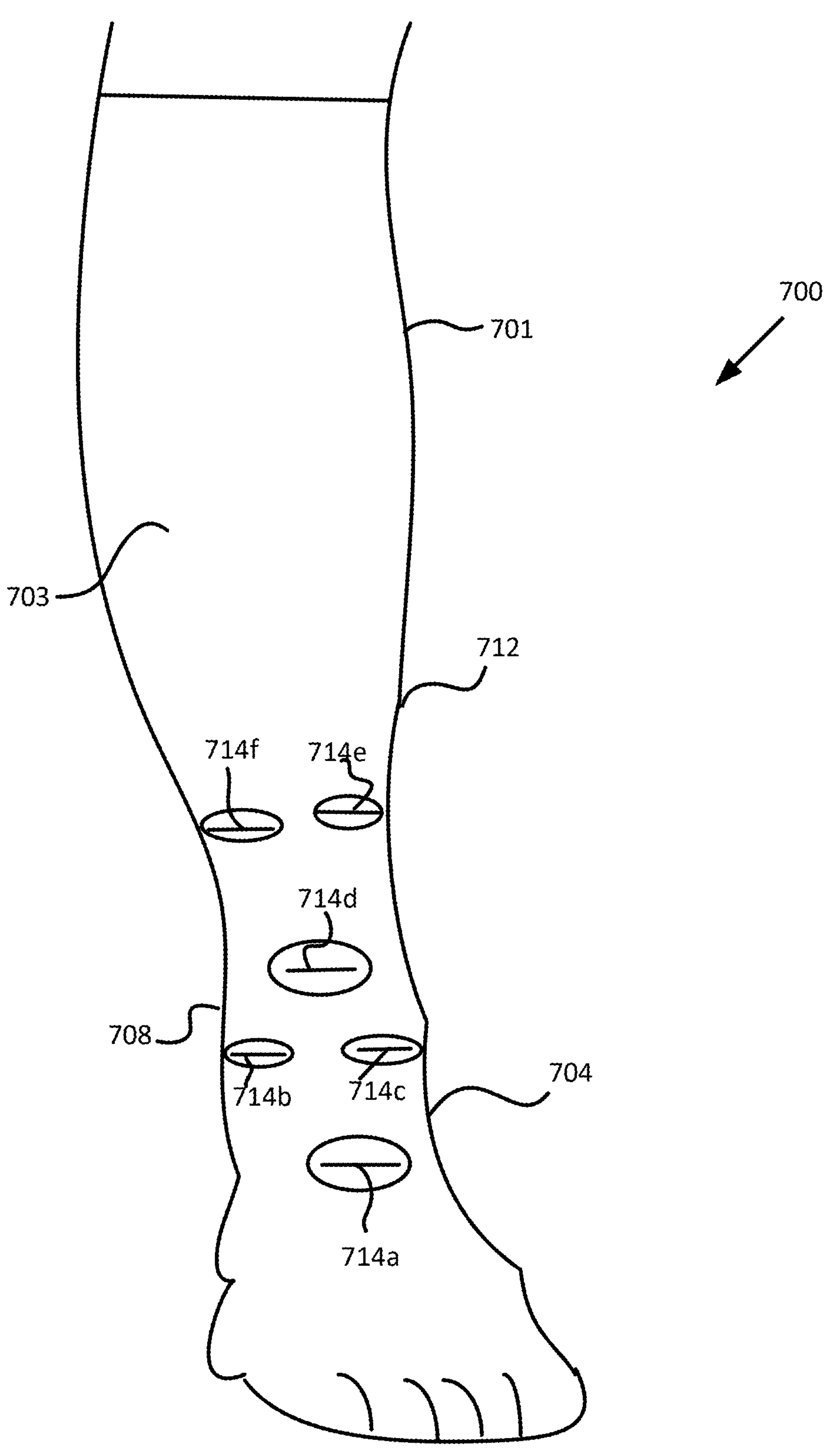
FIG. 15 is a perspective view of a compression sock in accordance with an embodiment of the present disclosure.

FIG. 15 is a perspective view of a compression sock in accordance with an embodiment of the present disclosure. The compression sock 700 may include a body 701 and first through $n^{th}$ sequential pulls (e.g., plurality of sequential pulls). The body 701 includes an inner face and an outer face 703. The plurality of sequential pulls may be a system to aid wearers (and those assisting them) in donning and doffing the compression sock 700. As shown in the present embodiment of FIG. 15, there are first through sixth sequential pulls 714*a-f*.

In various embodiments, the plurality of sequential pulls 714*a-f* may be coupled to the outer face 703. The plurality of sequential pulls 714*a-f* may be stitched, glued, tied, stuck, strapped, bound, clipped, grafted onto, or otherwise attached to the outer face 703. In various embodiments, the plurality of sequential pulls 714*a-f* may be in either a substantially vertical or substantially horizontal orientation relative the compression sock 700. In various aspects, the plurality of sequential pulls 714*a-f* may be cut into the outer face 703 and reinforced with stitching around the incisions to form the pulls 714*a-f*. In various embodiments, each of the plurality of sequential pulls 714*a-f* may be large enough to accommodate one or two fingers, or an aid hook, but small enough to avoid fabric bunching under footwear or clothing. In various embodiments, each of the plurality of sequential pulls 714*a-f* may range in width between 0.1 inches (in)-0.5 in, 0.5 in-0.75 in, 0.75 in-1 in, 1 in-2 in, or 2-3 in wide. In various embodiments, each of the plurality of sequential pulls 714*a-f* may range in thickness between 0.01 inches (in)-0.05 in, 0.05 in-0.10 in, 0.10 in-0.15 in, 0.15 in-0.2 in, 0.2 in-0.25 in, 0.25 in-0.3 in, or 0.3 in-0.5 in thick. In various embodiments, each of the plurality of sequential pulls 714*a-f* may be 0.25 in thick.

In various embodiments, the plurality of sequential pulls 714*a-f* may be placed along the body 701 of the compression sock 700 where the pulls 714*a-f* will create the most leverage (e.g., mechanical advantage) for the wearer, assistant, or an aid to pull the sock on and take the sock off (e.g., donning and doffing).

For instance, as shown, the body 701 includes a midfoot region 704, a hindfoot region 708, and a calf region 712. These regions correspond to regions of a typical human limb, the anatomy of which was described above in reference to FIGS. 2-4.

Each region is located proximal to at least one pull of the plurality of sequential pulls 714*a-f*.

For example, as shown, a first pull 714*a* is proximal the midfoot region 704 and specifically proximal the wearer's medial navicular, generating leverage in donning and doffing the compression sock 700 over the wearer's medial navicular. A second pull 714*b*, third pull 714*c*, and fourth pull 714*d* are proximal the hindfoot region 708, and specifically proximal the wearer's ankle mortise, generating leverage in donning and doffing the compression sock 700 over the wearer's ankle mortise.

Likewise, a fifth pull 714*e* and sixth pull 714*f* are located proximal the calf region 712 and may generate leverage in donning and doffing the compression sock 700 over the wearer's calf.

Figure 16:
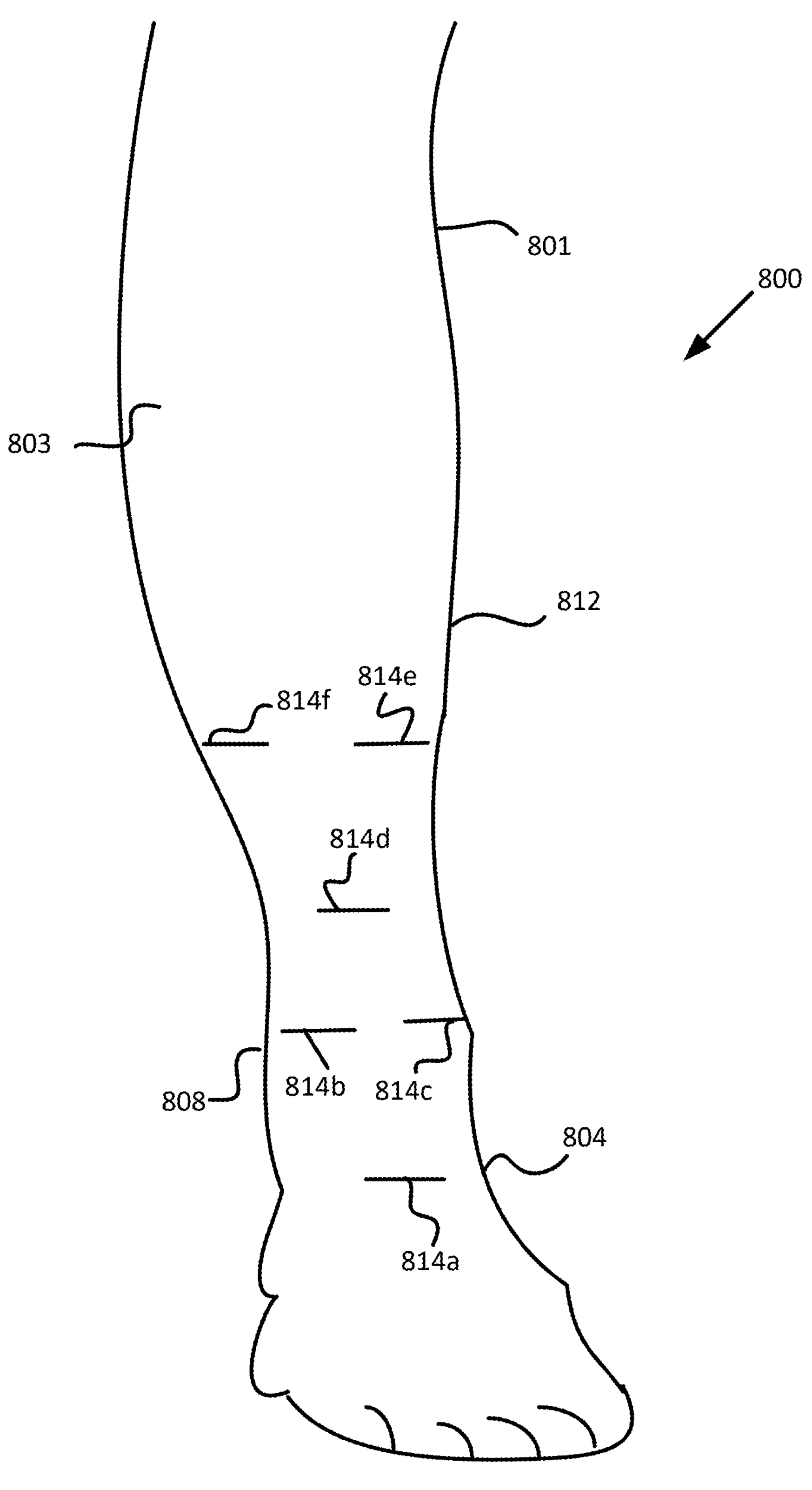
FIG. 16 is a perspective view of a compression sock in accordance with an embodiment of the present disclosure.

FIG. 16 is a perspective view of a compression sock in accordance with an embodiment of the present disclosure. The compression sock 800 may include a body 801 and first through $n^{th}$ sequential openings (e.g., plurality of sequential openings). The body 801 includes an inner face and an outer face 803. The plurality of sequential openings may be a system to aid wearers (and those assisting them) in donning and doffing the compression sock 800. As shown in the present embodiment of FIG. 16, there are first through sixth sequential pulls 814*a-f*.

In embodiments, the number of sequential openings is limited, as shown in FIG. 16, so that openings are only provided over or adjacent to specific regions of the leg when compression sock 800 is worn. This effectively limits the number of openings that may be formed, thereby limiting their placement to specific regions of the leg. If, for example, a large number of openings were to be placed all over compression sock 800, that could be problematic for the wearer.

Specifically, the locations of the openings for compression sock 800 are dictated by both anatomical necessity as well as physics to maximally reduce the force required to don the compression sock 800. The Law of Laplace dictates that the garment will be tightest over the narrowest anatomical areas, as expressed by the equation P=T/r, where P=Pressure exerted on the surface, T=Tension in the garment, and r=Radius of the curvature of the area being compressed.

Therefore, placing the openings as illustrated in FIG. 10 to release these areas significantly reduces the forces required to pull the garment into the proper position. The number of openings should be so limited so as to maintain the compression function of compression sock 800 (too many, or arbitrarily-placed openings would greatly weaken the compression sock, effectively rendering it unable to perform its function) and physical integrity-care must be taken to interrupt the textile of compression sock 800 as little as possible. Any additional openings will directly compromise the overall strength of compression sock 800, increasing the likelihood that it will rip.

The use of too many openings (e.g., openings formed in locations that don't play a role in assisting in the donning or removal of compression sock 800) will negatively affect the compressive capabilities of compression sock 800. Additionally, an overabundance of access openings may lead to blistering to the skin. As noted in Moffatt, C. J., O'Hare, L., & Mercier, G. (2020). Risks and Contraindications of Medical Compression Treatment. *Phlebology,* 35(4), 235-244, the skin moves differently in areas with different compression. This differential causes shear forces between the different areas and can lead to edema and significant blistering.

In various embodiments, the outer face 803 may define the plurality of sequential openings 814*a-f.* In various aspects, the plurality of sequential openings 814*a-f* may be cut into the outer face 803. In various aspects, the plurality of sequential openings 814*a-f* may be reinforced with stitching around the incisions that form the openings 814*a-f.* In various embodiments, the plurality of sequential openings 814*a-f* may be in either a substantially vertical or substantially horizontal orientation relative the compression sock 800. In various embodiments, each of the plurality of sequential openings 814*a-f* may be large enough to accommodate one or two fingers, or an aid hook, but small enough to avoid fabric bunching under footwear or clothing. In various embodiments, each of the plurality of sequential openings 814*a-f* may range in width between 0.1 inches (in)-0.5 in, 0.5 in-0.75 in, 0.75 in-1 in, 1 in-2 in, or 2-3 in wide.

In various embodiments, the plurality of sequential openings 814*a-f* may be placed along the body 801 of the compression sock 800 where the openings 814*a-f* will create the most leverage (e.g., mechanical advantage) for the wearer, assistant, or an aid to pull the sock on and take the sock off (e.g., donning and doffing).

For instance, as shown, the body 801 includes a midfoot region 804, a hindfoot region 808, and a calf region 812. These regions correspond to regions of a typical human limb, the anatomy of which was described above in reference to FIGS. 2-4.

Each region is located proximal to at least one opening of the plurality of sequential openings 814*a-f.*

For example, as shown, a first opening 814*a* is proximal the midfoot region 804 and specifically proximal the wearer's medial navicular, generating leverage in donning and doffing the compression sock 800 over the wearer's medial navicular. A second opening 814*b*, third opening 814*c*, and fourth opening 814*d* are proximal the hindfoot region 808, and specifically proximal the wearer's ankle mortise, generating leverage in donning and doffing the compression sock 800 over the wearer's ankle mortise.

Likewise, a fifth opening 814*e* and sixth opening 814*f* are located proximal the calf region 812 and may generate leverage in donning and doffing the compression sock 800 over the wearer's calf.

Figure 17:
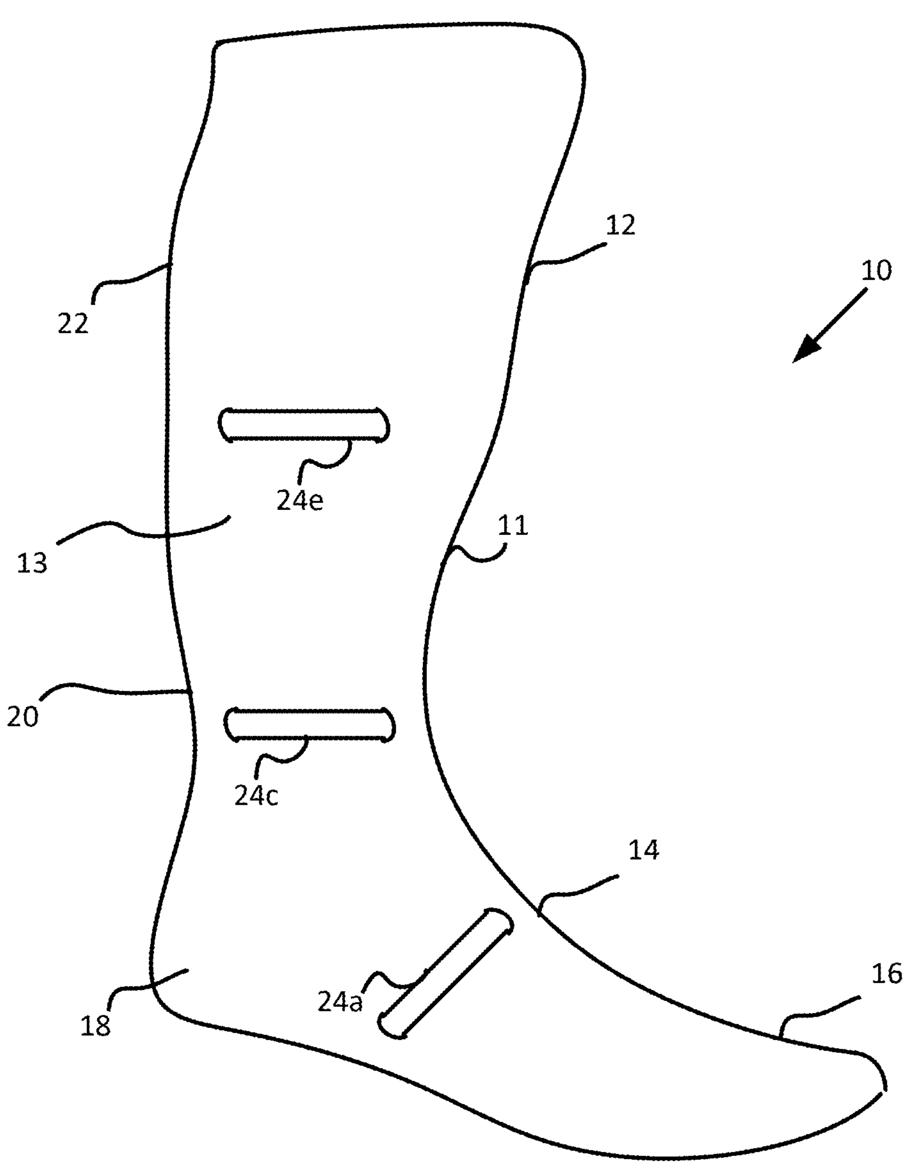
FIG. 17 is a perspective view of a compression sock in accordance with an embodiment of the present disclosure.
Figure 18:
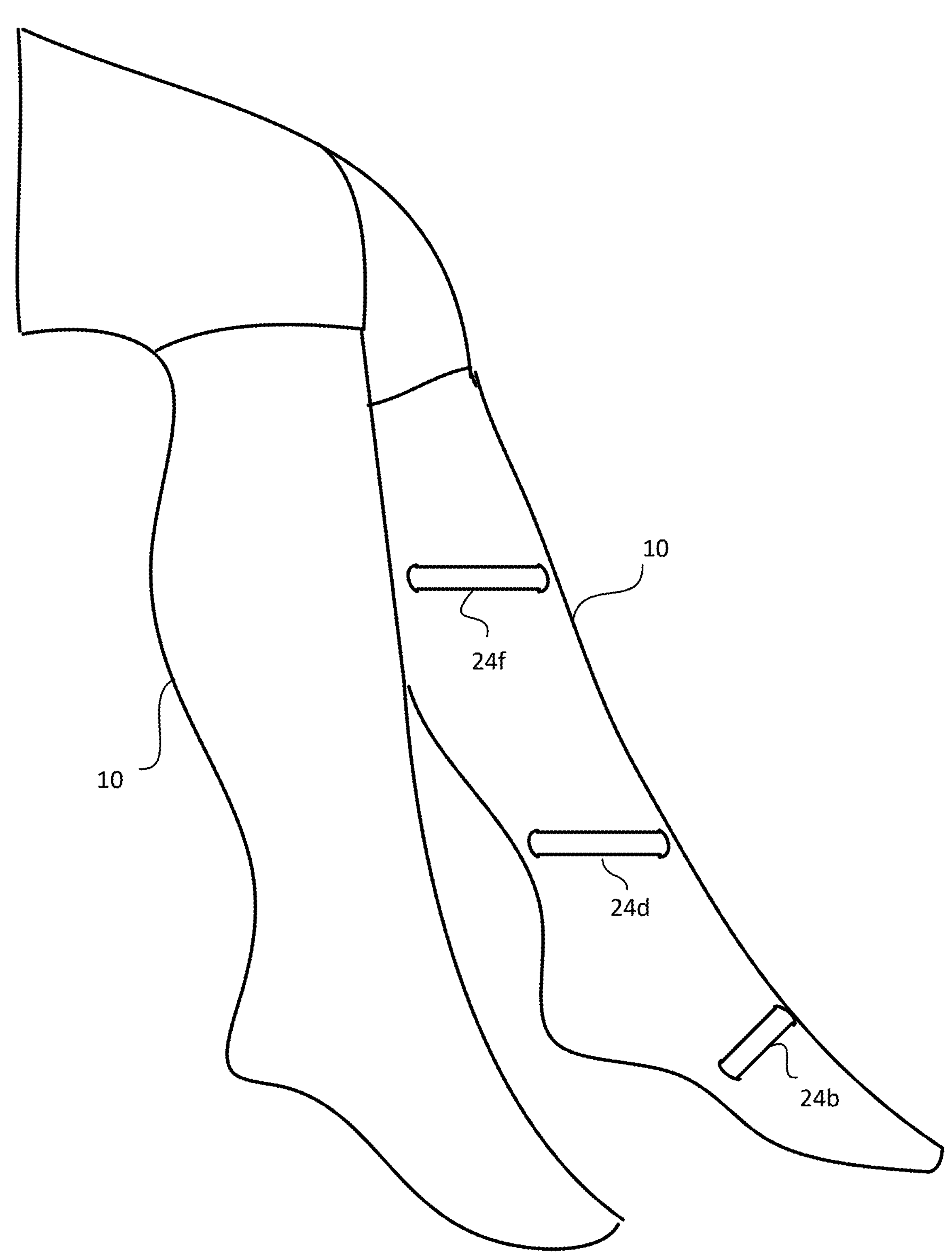
FIG. 18 is a perspective view of the compression sock of FIG. 17, as worn on both legs, in accordance with various embodiments.

FIG. 17 is a perspective view of a compression sock in accordance with an embodiment of the present disclosure. Moreover, FIG. 18 is a perspective view of the compression sock of FIG. 17, as worn on both legs. The wearer may be a patient afflicted with venous reflux resulting in lower leg swelling, skin changes and ulcerations. The wearer may be a user attempting to improve symptoms and mobility associated with venous disorders such as edema, phlebitis, and thrombosis. The wearer may be an athlete or user engaged in athletic activities, or a preventative care everyday user, or any user attempting to improve blood flow throughout the lower extremities. Accordingly, a compression sock 10 may have a strength ranging from 10-20 mm/Hg, 20-30 mm/Hg, 30-40 mm/Hg, and/or 40-50 mm/Hg.

The compression sock 10 may include a body 11 and first through $n^{th}$ sequential pulls (e.g., plurality of sequential pulls). The compression sock 10 may include any number of sequential pulls. The body 11 may include an inner face and an outer face 13. Generally, the inner face may be seen when the sock is turned inside out, given that the inner face is configured to interface with a wearer's anatomy when worn. Accordingly, the inner face may be a smooth uninterrupted surface configured to minimize irritation of the skin.

The plurality of sequential pulls may be a system to aid wearers (and those assisting them) in donning and doffing the compression sock 10. As shown in the present embodiment of FIGS. 17 and 18, there are first through sixth sequential pulls 24*a-f.*

In various embodiments, the plurality of sequential pulls 24*a-f* may be coupled to the outer face 13. In various embodiments, the plurality of sequential pulls 24*a-f* may be optionally coupled to any part of the outer face 13. The plurality of sequential pulls 24*a-f* may be stitched, glued, tied, stuck, strapped, bound, clipped, grafted onto, or otherwise attached to the outer face 13. In various embodiments, the plurality of sequential pulls 24*a-f* may be in either a substantially vertical or substantially horizontal orientation relative the compression sock 10. In various aspects, the plurality of sequential pulls 24*a-f* may be a plurality of rungs stitched to the outer face 13 and reinforced with stitching reinforcement or additional material to strengthen the attachment of the rung-like pulls 24*a-f* to the outer face 13.

In various embodiments, each of the plurality of sequential pulls 24*a-f* may be large enough to accommodate one to four fingers, or an aid hook, but small enough to avoid fabric bunching under footwear or clothing. In various embodiments, each of the plurality of sequential pulls 24*a-f* may range in width between 0.1 inches (in)-0.5 in, 0.5 in-0.75 in, 0.75 in-1 in, 1 in-2 in, 2-3 in, or 3-5 in wide. In various embodiments, each of the plurality of sequential pulls 24*a-f* may range in thickness between 0.01 inches (in)-0.05 in, 0.05 in-0.10 in, 0.10 in-0.15 in, 0.15 in-0.2 in, 0.2 in-0.25 in, 0.25 in-0.3 in, 0.3 in-0.5 in, or 0.5-1 in thick. In various embodiments, each of the plurality of sequential pulls 24*a-f* may be 0.5 in thick.

In various embodiments, the plurality of sequential pulls 24*a-f* may be placed along the body 11 of the compression sock 10 where the pulls 24*a-f* will create the most leverage (e.g., mechanical advantage) for the wearer, assistant, or an aid to pull the sock on and take the sock off (e.g., donning and doffing).

For instance, the body 11 includes a forefoot region 16, a midfoot region 14, a hindfoot region 18, a tendon region 20, a shin region 12, and a calf region 22. These regions correspond to regions of a typical human limb, the anatomy of which was described above in reference to FIGS. 2-4.

Each region is located proximal to at least one pull of the plurality of sequential pulls 24*a-f*. For example, in various embodiments, the forefoot region 16 of the body 11 is proximal a wearer's metatarsals. The midfoot region 14 is proximal a wearer's medial navicular and lateral cuboid. The hindfoot region 18 is proximal a wearer's medial malleolus, lateral malleolus, and heel. The tendon region 20 is proximal a wearer's Achilles tendon. The shin region 12 is proximal a wearer's medial tibial tuberosity and lateral tibial tuberosity. The calf region 22 is proximal a wearer's posterior calf.

As shown in FIGS. 17 and 18, a first pull 24*a* is proximal the midfoot region 14 and specifically proximal the wearer's lateral cuboid, generating leverage in donning and doffing the compression sock 10 over the wearer's lateral cuboid. This first pull 24*a* is also useful given that the midfoot region 14 is harder to grasp due to sock bunching that might occur at the forefoot region 16 proximal the wearer's phalanges and metatarsals. A second pull 24*b* is proximal the midfoot region 14 and specifically proximal the wearer's medial navicular, generating leverage in donning and doffing the compression sock 10 over the wearer's medial navicular. Likewise, a third pull 24*c* is located proximal the hindfoot region 18, and specifically proximate the wearer's lateral malleolus. The third pull 24*c* may generate leverage in donning and doffing the compression sock 10 over the wearer's lateral malleolus. Additionally, a fourth pull 24*d* is proximal the hindfoot region 18 and wearer's medial malleolus, generating leverage in donning and doffing the compression sock 10 over the wearer's medial malleolus. Being on either side of the ankle, the third pull 24*c* and fourth pull 24*d* are also proximate the heel, and together or on their own, may generate leverage in donning and doffing the compression sock 10 over the wearer's heel. Using both the third pull 24*c* and fourth pull 24*d* to generate leverage over the heel may be advantageous given that the heel represents the sharpest angular turn as the sock is pulled up the leg.

Similarly, a fifth pull 24*e* is located proximal the tendon region 20 and may generate leverage in donning and doffing the compression sock 10 over the wearer's Achilles tendon. A sixth pull 24*f* is located proximal the shin region 12 and wearer's medial tibial tuberosity and may generate leverage in donning and doffing the compression sock 10 over the wearer's medial tibial tuberosity.

Accordingly, as the wearer, assistant, or aid is pulling the sock 10 over the wearer's leg, the pulls 24*a-f* may be manipulated in sequential order, thus generating sufficient leverage to pull the compression sock 10 over parts of the anatomy that challenge those with limited mobility and/or grip strength. Moreover, the width of the pulls 24*a-f* and where each pull is attached at the outer face 13 (e.g., the part of the compression sock 10 that releases) may aid in improving case of donning the compression sock 10.

In various embodiments, the compression sock 10 may be made of any suitable compressive fabric, including elastane, cotton, microfiber, and the like, and composites thereof. In various embodiments, the plurality of sequential pulls 24*a-f* may be made of the same compressive fabric as the compression sock 10. In other embodiments, the plurality of sequential pulls 24*a-f* may be made of a different fabric from the compression sock 10. In various embodiments, the plurality of sequential pulls 24*a-f* may be made of any fabric, such as polyester, nylon, elastane, and the like, and composites thereof, or any fabric wherein a total deformation of the plurality of sequential pulls 24*a-f* is substantially similar to that of the compression sock 10 fabric. In various embodiments, the plurality of sequential pulls 24*a-f* may be made of any fabric that increases the compression sock's ability to stretch.

Figure 19:
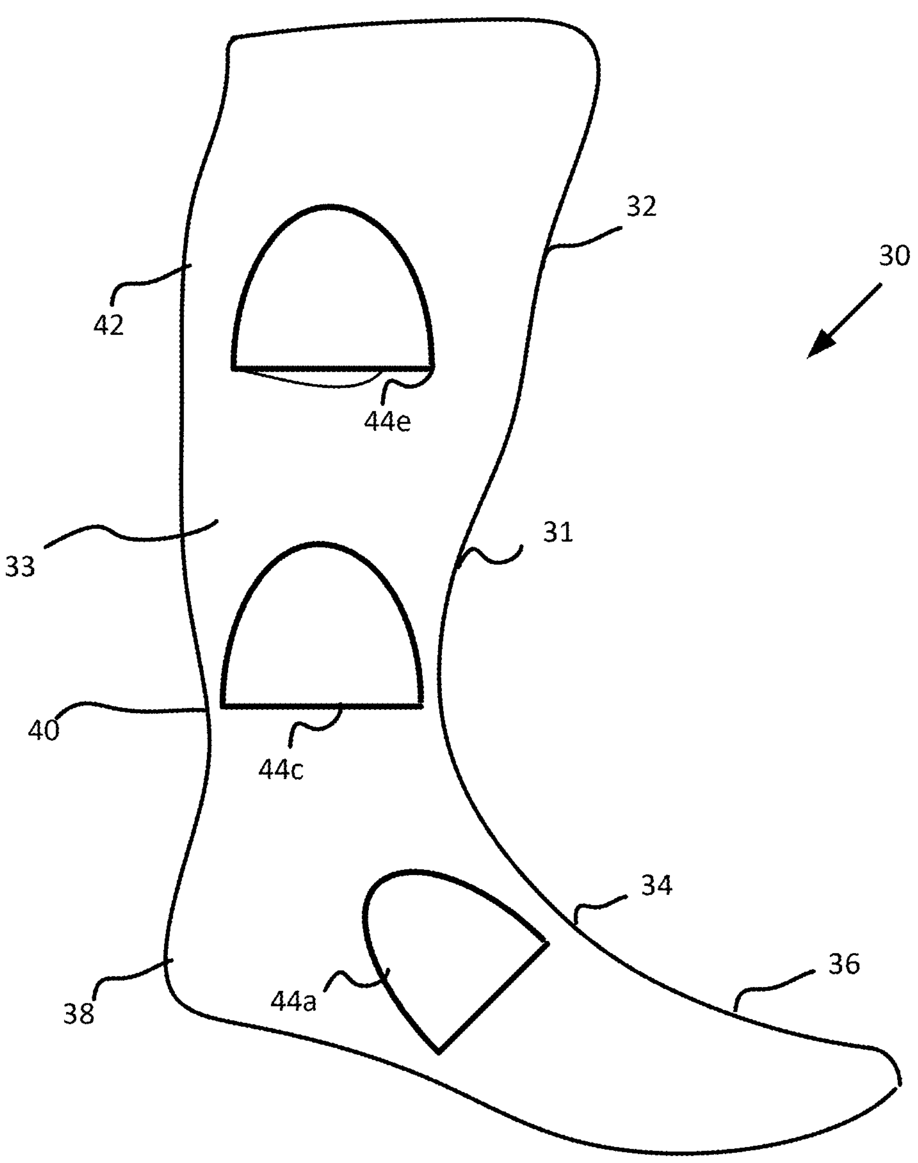
FIG. 19 is a perspective view of a compression sock in accordance with an embodiment of the present disclosure.
Figure 20:
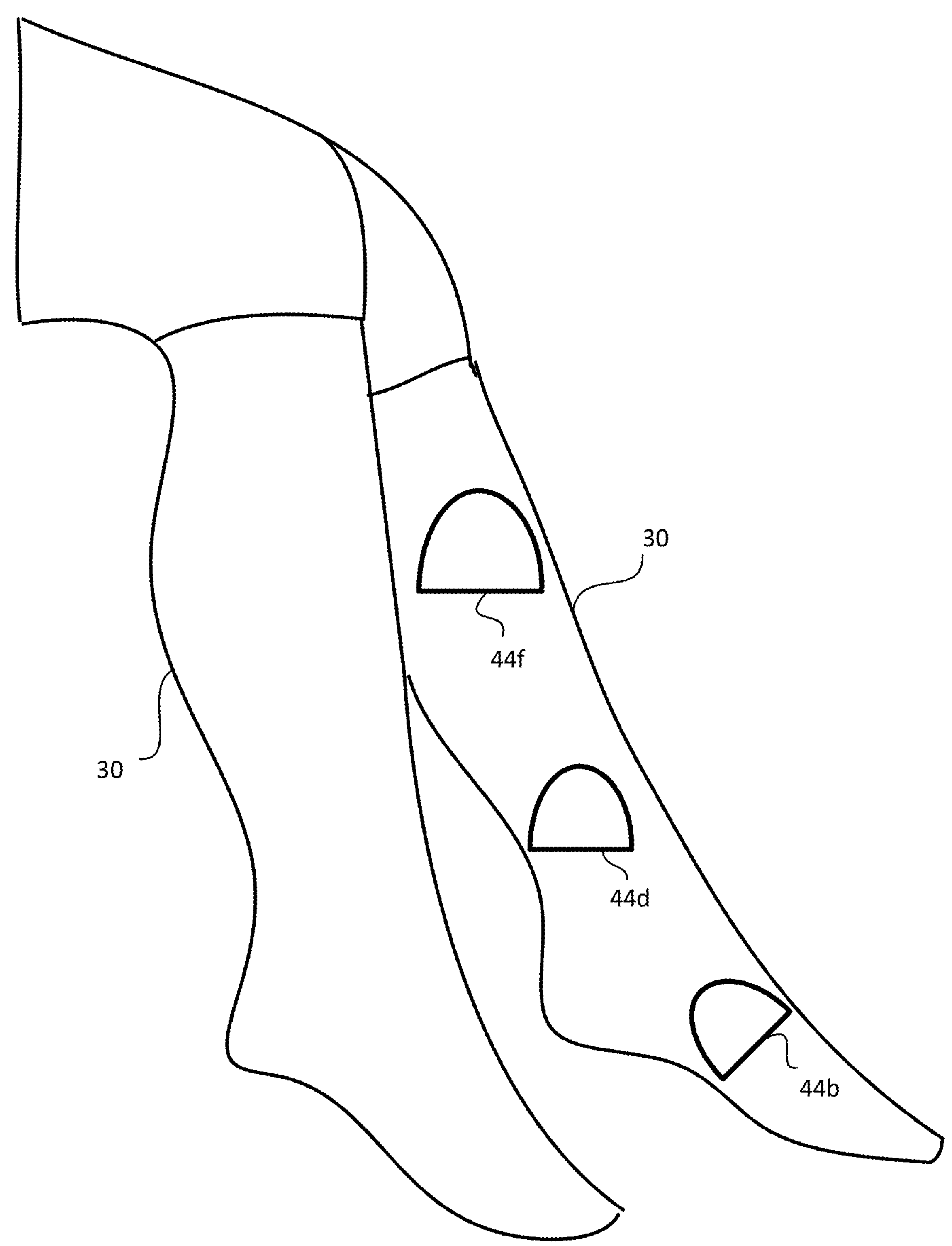
FIG. 20 is a perspective view of the compression sock of FIG. 19, as worn on both legs, in accordance with various embodiments.

FIG. 19 is a perspective view of a compression sock in accordance with an embodiment of the present disclosure. Moreover, FIG. 20 is a perspective view of the compression sock of FIG. 19, as worn on both legs. The wearer may be a patient afflicted with venous reflux resulting in lower leg swelling, skin changes and ulcerations. The wearer may be a user attempting to improve symptoms and mobility associated with venous disorders such as edema, phlebitis, and thrombosis. The wearer may be an athlete or user engaged in athletic activities, or a preventative care everyday user, or any user attempting to improve blood flow throughout the lower extremities. Accordingly, a compression sock 30 may have a strength ranging from 10-20 mm/Hg, 20-30 mm/Hg, 30-40 mm/Hg, and/or 40-50 mm/Hg.

The compression sock 30 may include a body 31 defining first through n$^{th}$ sequential grips (e.g., plurality of sequential grips). The compression sock 30 may include a body 31 defining any number of sequential grips. The body 31 includes an inner face and an outer face 33. Generally, the inner face may be seen when the sock is turned inside out, given that the inner face is configured to interface with a wearer's anatomy when worn. Accordingly, the inner face may be a smooth uninterrupted surface configured to minimize irritation of the skin.

The plurality of sequential grips may be a system to aid wearers (and those assisting them) in donning and doffing the compression sock 30. As shown in the present embodiment of FIGS. 19 and 20, there are first through sixth sequential grips 44*a-f*.

In various embodiments, the outer face 33 may define the plurality of sequential grips 44*a-f*. In various embodiments, the outer face 33 may optionally define the plurality of sequential grips 44*a-f* at any part of the outer face 33. In various embodiments, the plurality of sequential grips 44*a-f* may be in either a substantially vertical or substantially horizontal orientation relative the compression sock 30. In various embodiments, excess material of the outer face 33 may define the plurality of sequential grips 44*a-f*. In various aspects, the plurality of sequential grips 44*a-f* may be cut into the outer face 33. In various aspects, the plurality of sequential grips 44*a-f* may be reinforced with stitching around the incisions in the outer face 33.

In various embodiments, each of the plurality of sequential grips 44*a-f* may be large enough to accommodate one to four fingers, or an aid hook, but small enough to avoid fabric bunching under footwear or clothing. In various embodiments, each of the plurality of sequential grips 44*a-f* may range in width between 0.1 inches (in)-0.5 in, 0.5 in-0.75 in, 0.75 in-1 in, 1 in-2 in, 2-3 in, or 3-5 in wide. In various embodiments, each of the plurality of sequential grips 44*a-f* may range in thickness between 0.01 inches (in)-0.05 in, 0.05 in-0.10 in, 0.10 in-0.15 in, 0.15 in-0.2 in, 0.2 in-0.25 in, 0.25 in-0.3 in, 0.3 in-0.5 in, or 0.5-1 in thick. In various embodiments, each of the plurality of sequential grips 44*a-f* may be 0.5 in thick.

In various embodiments, the plurality of sequential grips 44*a-f* may be defined along the body 31 of the compression sock 30 where the grips 44*a-f* will create the most leverage (e.g., mechanical advantage) for the wearer, assistant, or an aid to pull the sock on and take the sock off (e.g., donning and doffing).

For instance, the body 31 includes a forefoot region 36, a midfoot region 34, a hindfoot region 38, a tendon region 40, a shin region 32, and a calf region 42. These regions correspond to regions of a typical human limb, the anatomy of which was described above in reference to FIGS. 2-4.

Each region is located proximal to at least one grip of the plurality of sequential grips 44*a-f*. For example, in various embodiments, the forefoot region 36 of the body 31 is proximal a wearer's metatarsals. The midfoot region 34 is proximal a wearer's medial navicular and lateral cuboid. The hindfoot region 38 is proximal a wearer's medial malleolus, lateral malleolus, and heel. The tendon region 40 is proximal a wearer's Achilles tendon. The shin region 32 is proximal a wearer's medial tibial tuberosity and lateral tibial tuberosity. The calf region 42 is proximal a wearer's posterior calf.

As shown in FIGS. 19 and 20, a first grip 44*a* is proximal the midfoot region 34 and specifically proximal the wearer's lateral cuboid, generating leverage in donning and doffing the compression sock 30 over the wearer's lateral cuboid. This first grip 44*a* is also useful given that the midfoot region 34 is harder to grasp due to sock bunching that might occur at the forefoot region 36 proximal the wearer's phalanges and metatarsals. A second grip 44*b* is proximal the midfoot region 34 and specifically proximal the wearer's medial navicular, generating leverage in donning and doffing the compression sock 30 over the wearer's medial navicular. Likewise, a third grip 44*c* is located proximal the hindfoot region 38, and specifically proximate the wearer's lateral malleolus. The third grip 44*c* may generate leverage in donning and doffing the compression sock 30 over the wearer's lateral malleolus. Additionally, a fourth grip 44*d* is proximal the hindfoot region 38 and wearer's medial malleolus, generating leverage in donning and doffing the compression sock 30 over the wearer's medial malleolus. Being on either side of the ankle, the third grip 44*c* and fourth grip 44*d* are also proximate the heel, and together or on their own, may generate leverage in donning and doffing the compression sock 30 over the wearer's heel. Using both the third grip 44*c* and fourth grip 44*d* to generate leverage over the heel may be advantageous given that the heel represents the sharpest angular turn as the sock is pulled up the leg.

Similarly, a fifth grip 44*c* is located proximal the tendon region 40 and may generate leverage in donning and doffing the compression sock 30 over the wearer's Achilles tendon. A sixth grip 44*f* is located proximal the shin region 32 and wearer's medial tibial tuberosity and may generate leverage in donning and doffing the compression sock 30 over the wearer's medial tibial tuberosity.

Accordingly, as the wearer, assistant, or aid is pulling the sock 30 over the wearer's leg, the grips 44*a-f* may be manipulated in sequential order, thus generating sufficient leverage to pull the compression sock 30 over parts of the anatomy that challenge those with limited mobility and/or grip strength. Moreover, the width of the grips 44*a-f* and where each grip is defined by the outer face 33 (e.g., the part of the compression sock 30 that releases) may aid in improving case of donning the compression sock 30.

In various embodiments, the compression sock 30 may be made of any suitable compressive fabric, including elastane, cotton, microfiber, and the like, and composites thereof. In various embodiments, the plurality of sequential grips 44*a-f* may be made of the same compressive fabric as the compression sock 30. In other embodiments, the plurality of sequential grips 44*a-f* may be made of a different fabric from the compression sock 30. In various embodiments, the plurality of sequential grips 44*a-f* may be made of any fabric, such as polyester, nylon, elastane, and the like, and composites thereof, or any fabric wherein a total deformation of the plurality of sequential grips 44*a-f* is substantially similar to that of the compression sock 30 fabric. In various embodiments, the plurality of sequential grips 44*a-f* may be made of any fabric that increases the compression sock's ability to stretch.

Figure 21:
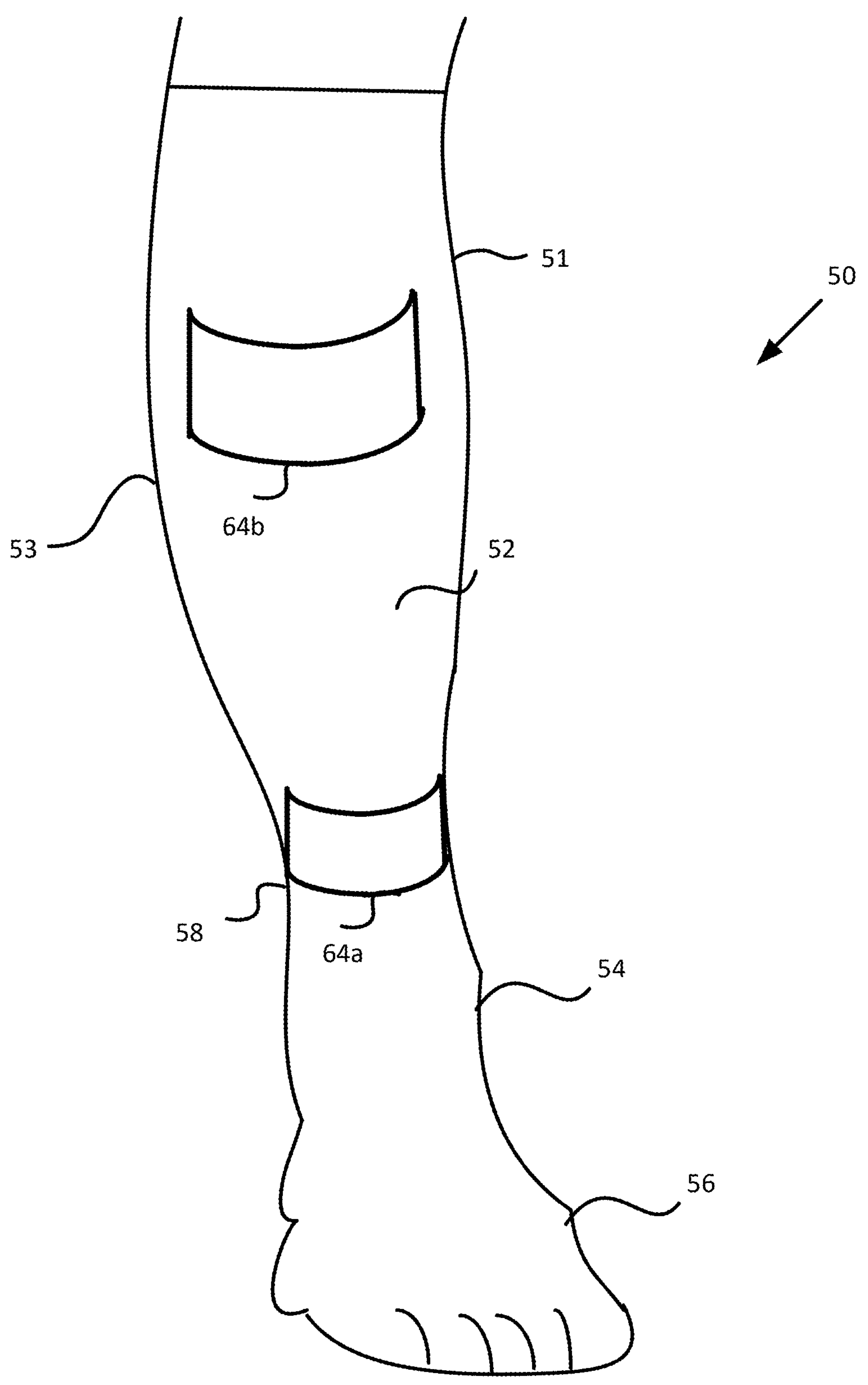
FIG. 21 is a perspective view of a compression sock in accordance with an embodiment of the present disclosure.
Figure 22:
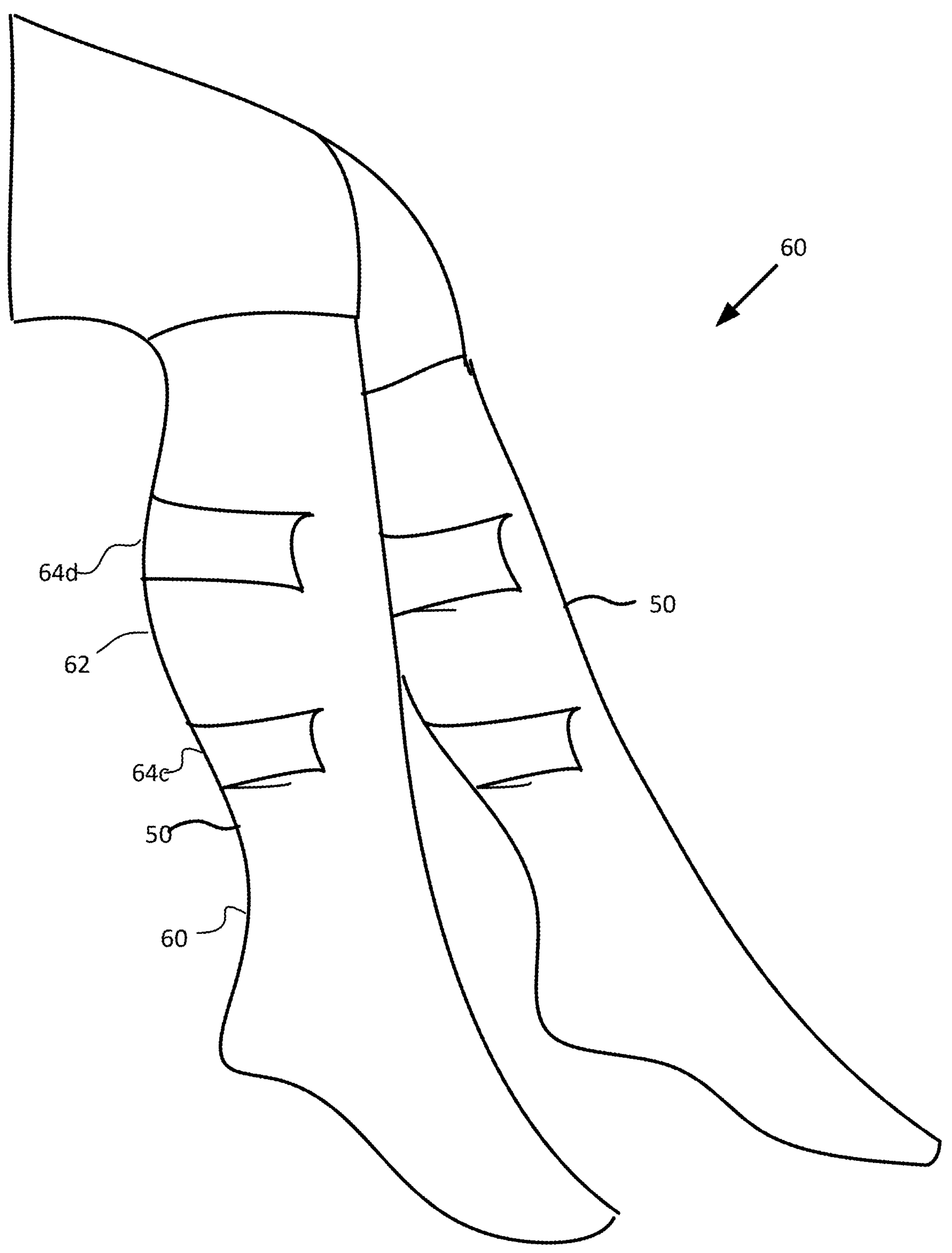
FIG. 22 is a perspective view of the compression sock of FIG. 21, as worn on both legs, in accordance with various embodiments.

FIG. 21 is a perspective view of a compression sock in accordance with an embodiment of the present disclosure. Moreover, FIG. 22 is a perspective view of the compression sock of FIG. 21, as worn on both legs. The wearer may be a patient afflicted with venous reflux resulting in lower leg swelling, skin changes and ulcerations. The wearer may be a user attempting to improve symptoms and mobility associated with venous disorders such as edema, phlebitis, and thrombosis. The wearer may be an athlete or user engaged in athletic activities, or a preventative care everyday user, or any user attempting to improve blood flow throughout the lower extremities. Accordingly, a compression sock 50 may have a strength ranging from 10-20 mm/Hg, 20-30 mm/Hg, 30-40 mm/Hg, and/or 40-50 mm/Hg.

The compression sock 50 may include a body 51 defining first through $n^{th}$ sequential grips (e.g., plurality of sequential grips). The compression sock 50 may include a body 51 defining any number of sequential grips. The body 51 includes an inner face and an outer face 53. Generally, the inner face may be seen when the sock is turned inside out, given that the inner face is configured to interface with a wearer's anatomy when worn. Accordingly, the inner face may be a smooth uninterrupted surface configured to minimize irritation of the skin.

The plurality of sequential grips may be a system to aid wearers (and those assisting them) in donning and doffing the compression sock 50. As shown in the present embodiment of FIGS. 21 and 22, there are first through fourth sequential grips 64*a-d*.

In various embodiments, the outer face 53 may define the plurality of sequential grips 64*a-d*. In various embodiments, the outer face 53 may optionally define the plurality of sequential grips 64*a-d* at any part of the outer face 53. In various embodiments, excess material of the outer face 53 may define the plurality of sequential grips 64*a-d*. In various aspects, the plurality of sequential grips 64*a-d* may be cut into the outer face 53. In various aspects, the plurality of sequential grips 64*a-d* may be reinforced with stitching around the incisions in the outer face 53. In various embodiments, the plurality of sequential grips 64*a-d* may be in either a substantially vertical or substantially horizontal orientation relative the compression sock 50.

In various embodiments, each of the plurality of sequential grips 64*a-d* may be large enough to accommodate one to four fingers, or an aid hook, but small enough to avoid fabric bunching under footwear or clothing. In various embodiments, each of the plurality of sequential grips 64*a-d* may range in width between 0.1 inches (in)-0.5 in, 0.5 in-0.75 in, 0.75 in-1 in, 1 in-2 in, 2-3 in, or 3-5 in wide. In various embodiments, each of the plurality of sequential grips 64*a-d* may range in thickness between 0.01 inches (in)-0.05 in, 0.05 in-0.10 in, 0.10 in-0.15 in, 0.15 in-0.2 in, 0.2 in-0.25 in, 0.25 in-0.3 in, 0.3 in-0.5 in, or 0.5-1 in thick. In various embodiments, each of the plurality of sequential grips 64*a-d* may be 0.5 in thick.

In various embodiments, the plurality of sequential grips 64*a-d* may be defined along the body 51 of the compression sock 50 where the grips 64*a-d* will create the most leverage (e.g., mechanical advantage) for the wearer, assistant, or an aid to pull the sock on and take the sock off (e.g., donning and doffing).

For instance, the body 51 includes a forefoot region 56, midfoot region 54, a hindfoot region 58, a tendon region 60, a shin region 52, and a calf region 62. These regions correspond to regions of a typical human limb, the anatomy of which was described above in reference to FIGS. 2-4.

Each region is located proximal to at least one grip of the plurality of sequential grips 64*a-d*. For example, in various embodiments, the forefoot region 56 of the body 51 is proximal a wearer's metatarsals. The midfoot region 54 is proximal a wearer's medial navicular and lateral cuboid. The hindfoot region 58 is proximal a wearer's medial malleolus, lateral malleolus, and heel. The tendon region 60 is proximal a wearer's Achilles tendon. The shin region 52 is proximal a wearer's medial tibial tuberosity and lateral tibial tuberosity. The calf region 62 is proximal a wearer's posterior calf.

As shown in FIGS. 21 and 22, a first grip 64*a* is proximal the midfoot region 54, generating leverage in donning and doffing the compression sock 50 over the wearer's midfoot region. This first grip 64*a* is also useful given that the midfoot region 54 is harder to grasp due to sock bunching that might occur at the forefoot region 56 proximal the wearer's phalanges and metatarsals. A second grip 64*b* is proximal the shin region 52, generating leverage in donning and doffing the compression sock 50 up and down the wearer's leg. Likewise, a third grip 64*c* is located proximal the hindfoot region 58 and the tendon region 60, and may generate leverage in donning and doffing the compression sock 50 over the wearer's heel and up the Achilles tendon. This may be advantageous given that the heel represents the sharpest angular turn as the sock is pulled up the leg. Similarly, a fourth grip 64*d* is located proximal the calf region 62 and may generate leverage in donning and doffing the compression sock 50 over the wearer's posterior calf.

Accordingly, as the wearer, assistant, or aid is pulling the sock 50 over the wearer's leg, the grips 64*a-d* may be manipulated in sequential order, thus generating sufficient leverage to pull the compression sock 50 over parts of the anatomy that challenge those with limited mobility and/or grip strength. Moreover, the width of the grips 64*a-d* and where each grip is defined by the outer face 53 (e.g., the part of the compression sock 50 that releases) may aid in improving case of donning the compression sock 50.

In various embodiments, the compression sock 50 may be made of any suitable compressive fabric, including elastane, cotton, microfiber, and the like, and composites thereof. In various embodiments, the plurality of sequential grips 64*a-d* may be made of the same compressive fabric as the compression sock 50. In other embodiments, the plurality of sequential grips 64*a-d* may be made of a different fabric from the compression sock 50. In various embodiments, the plurality of sequential grips 44*a-f* may be made of any fabric, such as polyester, nylon, elastane, and the like, and composites thereof, or any fabric wherein a total deformation of the plurality of sequential grips 64*a-d* is substantially similar to that of the compression sock 50 fabric. In various embodiments, the plurality of sequential grips 64*a-d* may be made of any fabric that increases the compression sock's ability to stretch.

In some aspects, the techniques described herein relate to a compression sock configured to be worn by a wearer. The compression sock may include a body having an inner face and an outer face. The inner face may be a smooth surface interfacing with a wearer's anatomy. The body may further include a forefoot region, a midfoot region, a hindfoot region, a tendon region, a shin region, and a calf region. The compression sock may further include a plurality of sequential pulls coupled to the outer face of the body. At least one pull may be located proximal each region. Moreover, each pull may generate leverage for the wearer donning and doffing the compression sock. Accordingly, the plurality of sequential pulls may aid in donning and doffing the compression sock.

In some aspects, the techniques described herein relate to a compression sock configured to be worn by a wearer. The compression sock may include a body having an inner face and an outer face. The inner face may be a smooth surface interfacing with a wearer's anatomy. The body may further include a forefoot region, a midfoot region, a hindfoot region, a tendon region, a shin region, and a calf region. The outer face of the body of the compression sock may define a plurality of sequential openings. At least one opening may be located proximal each region. Moreover, each opening may generate leverage for the wearer donning and doffing the compression sock. Accordingly, the plurality of sequential openings may aid in donning and doffing the compression sock.

In some aspects, the techniques described herein relate to a compression sock configured to be worn by a wearer. The compression sock may comprise regions of graduated compression. In some aspects, of the regions of graduated compression, the ankle region may comprise greater compression force (e.g., pressure) than other regions. Such graduated compression may be advantageous for wearers seeking medical-grade compression.

In some aspects, the techniques described herein relate to a compression sock configured to be worn by a wearer. The compression sock may comprise regions of progressive compression. In some aspects, of the regions of progressive compression, the calf region may comprise greater compression force (e.g., pressure) than other regions. Such progressive compression may be advantageous for wearers seeking to improve calf muscle circulation and pumping for various purposes, such as for example, sports activity.

The inventor has contemplated that these systems could be used on any compression sequencing scheme.

The above is presented to describe specific attributes of this invention. The inventor has contemplated that these systems could be used within any garment that has stretch, compression, stiffness to the textile or is otherwise difficult to don. The inventor has contemplated that these systems could be used on compression socks, and/or garments other than compression socks, e.g., pneumatic and non-pneumatic (lymphedema decompression systems). This description is not meant to limit the scope of this disclosure.

The invention will be especially pertinent to those with grip strength dysfunction such as those with a history of stroke, rheumatoid arthritis, or the like. These systems will also be especially useful for anyone who has limited range of motion. These systems will also help any patients, including patients who have lost strength and flexibility due to age. These systems will also help caregivers who have difficulty gaining grip and leverage. Anyone who benefits from these types of garments will benefit from this invention. Anyone who aids another person who wears these types of garments will benefit from this invention.

The preceding detailed description is merely illustrative in nature and is not intended to limit the embodiments of the subject matter or the application and uses of such embodiments.

As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, or detailed description.

The connecting lines shown in the various figures contained herein are intended to represent exemplary functional relationships and/or physical couplings between the various elements. It should be noted that many alternative or additional functional relationships or physical connections may be present in an embodiment of the subject matter. In addition, certain terminology may also be used herein for the purpose of reference only, and thus are not intended to be limiting, and the terms "first", "second" and other such numerical terms referring to structures do not imply a sequence or order unless clearly indicated by the context.

The foregoing description refers to elements or nodes or features being "connected" or "coupled" together. As used herein, unless expressly stated otherwise, "connected" means that one element is directly joined to (or directly communicates with) another element, and not necessarily mechanically. Likewise, unless expressly stated otherwise, "coupled" means that one element is directly or indirectly joined to (or directly or indirectly communicates with, electrically or otherwise) another element, and not necessarily mechanically. Thus, although the schematic shown in the figures depict one exemplary arrangement of elements, additional intervening elements, devices, features, or components may be present in an embodiment of the depicted subject matter.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A compression sock configured to be worn by a wearer, comprising:

a body comprising an inner face and an outer face, the inner face configured to interface with a wearer's anatomy, the body comprising an elastic material configured to apply a compressive force to a foot and calf of the wearer, the body including:

a forefoot region;

a midfoot region;

a hindfoot region;

a tendon region;

a shin region;

and a calf region; and a plurality of sequential pulls coupled to the outer face of the body, at least one pull located proximal each region, and wherein each pull includes an opening in the compression sock and is configured to generate leverage for the wearer donning and doffing the compression sock, wherein the forefoot region is configured to be proximal a wearer's metatarsals, wherein a first pull is proximal the forefoot region and is configured to generate leverage for the wearer donning and doffing the compression sock over the wearer's metatarsals, wherein the midfoot region is configured to be proximal a wearer's medial navicular, wherein a second pull is proximal the midfoot region and is configured to generate leverage for the wearer donning and doffing the compression sock over the wearer's medial navicular, wherein the midfoot region is configured to be proximal a wearer's lateral cuboid, wherein a third pull is proximal the midfoot region and is configured to generate leverage for the wearer donning and doffing the compression sock over the wearer's lateral cuboid, wherein the hindfoot region is configured to be proximal a wearer's medial malleolus, wherein a fourth pull is proximal the hindfoot region and is configured to generate leverage for the wearer donning and doffing the compression sock over the wearer's medial malleolus, wherein the hindfoot region is configured to be proximal a wearer's lateral malleolus, wherein a fifth pull is located proximal the hindfoot region and is configured to generate leverage for the wearer donning and doffing the compression sock over the wearer's lateral malleolus, wherein the tendon region is configured to be proximal a wearer's Achilles tendon, wherein a sixth pull is located proximal the tendon region and is configured to generate leverage for the wearer donning and doffing the compression sock over the wearer's Achilles tendon, wherein the shin region is configured to be proximal a wearer's medial tibial tuberosity, wherein a seventh pull is located proximal the shin region and is configured to generate leverage for the wearer donning and doffing the compression sock over the wearer's medial tibial tuberosity, wherein the shin region is configured to be proximal a wearer's lateral tibial tuberosity, wherein an eighth pull is located proximal the shin region and is configured to generate leverage for the wearer donning and doffing the compression sock over the wearer's lateral tibial tuberosity, wherein the calf region is configured to be proximal a wearer's posterior calf, wherein a ninth pull is located proximal the calf region and is configured to generate leverage for the wearer donning and doffing the compression sock over the wearer's posterior calf.

2. The compression sock of claim 1, wherein each of the plurality of sequential pulls is 0.75 inches (in) wide.

3. The compression sock of claim 1, wherein each pull is 0.25 inches (in) thick.

4. The compression sock of claim 1, wherein the body is made of an elastane.

5. The compression sock of claim 1, wherein each pull is made of nylon.

6. The compression sock of claim 1, wherein each pull is made of an elastane.

7. A compression sock configured to be worn by a wearer, comprising:

a body comprising an inner face and an outer face, the inner face configured to interface with a wearer's anatomy, the body further comprising:

a forefoot region;

a midfoot region;

a hindfoot region;

a tendon region;

a shin region;

and a calf region, wherein the outer face of the body defines a plurality of sequential openings, at least one opening located proximal each region, and wherein each opening is configured to generate leverage for the wearer donning and doffing the compression sock, wherein the forefoot region is configured to be proximal a wearer's metatarsals, wherein a first opening is proximal the forefoot region and is configured to generate leverage for the wearer donning and doffing the compression sock over the wearer's metatarsals, wherein the midfoot region is configured to be proximal a wearer's medial navicular and lateral cuboid, wherein a second opening is proximal the midfoot region and is configured to generate leverage for the wearer donning and doffing the compression sock over the wearer's medial navicular, wherein a third opening is proximal the midfoot region and is configured to generate leverage for the wearer donning and doffing the compression sock over the wearer's lateral cuboid, wherein the hindfoot region is configured to be proximal a wearer's medial malleolus and lateral malleolus, wherein a fourth opening is proximal the hindfoot region and is configured to generate leverage for the wearer donning and doffing the compression sock over the wearer's medial malleolus, wherein a fifth opening is located proximal the hindfoot region and is configured to generate leverage for the wearer donning and doffing the compression sock over the wearer's lateral malleolus, wherein the tendon region is configured to be proximal a wearer's Achilles tendon, wherein a sixth opening is located proximal the tendon region and is configured to generate leverage for the wearer donning and doffing the compression sock over the wearer's Achilles tendon, wherein the shin region is configured to be proximal a wearer's medial tibial tuberosity, wherein a seventh opening is located proximal the shin region and is configured to generate leverage for the wearer donning and doffing the compression sock over the wearer's medial tibial tuberosity, wherein the calf region is configured to be proximal a wearer's posterior calf, wherein a ninth opening is located proximal the calf region and is configured to generate leverage for the wearer donning and doffing the compression sock over the wearer's posterior calf.

* * * * *